United States Patent
Zhang et al.

(10) Patent No.: US 9,320,593 B2
(45) Date of Patent: Apr. 26, 2016

(54) SYSTEMS AND METHODS FOR PLANNING HAIR TRANSPLANTATION

(71) Applicant: Restoration Robotics, Inc., San Jose, CA (US)

(72) Inventors: Hui Zhang, San Jose, CA (US); Mohan Bodduluri, Palo Alto, CA (US); Gabriele Zingaretti, Aptos, CA (US); Theodore Thuong Nguyen, San Jose, CA (US)

(73) Assignee: Restoration Robotics, Inc., San Jose, CA (US)

( * ) Notice: Subject to any disclaimer, the term of this patent is extended or adjusted under 35 U.S.C. 154(b) by 497 days.

(21) Appl. No.: 13/844,317

(22) Filed: Mar. 15, 2013

(65) Prior Publication Data

US 2014/0261467 A1    Sep. 18, 2014

(51) Int. Cl.
| | | |
|---|---|---|
| *G06K 9/00* | (2006.01) | |
| *A61F 2/10* | (2006.01) | |
| *A61B 19/00* | (2006.01) | |
| *A61B 17/50* | (2006.01) | |

(52) U.S. Cl.
CPC . *A61F 2/10* (2013.01); *A61B 19/50* (2013.01); *A61B 2019/505* (2013.01)

(58) Field of Classification Search
CPC ................................ A61B 19/00; G06F 19/00
USPC .................. 382/128–134; 606/130, 133, 187; 128/898; 703/11
See application file for complete search history.

(56) References Cited

U.S. PATENT DOCUMENTS

| | | | |
|---|---|---|---|
| 4,807,163 A | 2/1989 | Gibbons | |
| 5,060,171 A | 10/1991 | Steir et al. | |
| 5,687,259 A | 11/1997 | Linford | |
| 6,081,611 A | 6/2000 | Linford et al. | |
| 6,445,943 B1 | 9/2002 | Ferre et al. | |
| 6,572,625 B1 * | 6/2003 | Rassman .......... | A61B 17/32053 606/133 |
| 6,585,746 B2 * | 7/2003 | Gildenberg ...... | A61B 17/32053 606/187 |
| 7,083,611 B2 * | 8/2006 | Lemchen ............ | A61B 18/203 128/898 |
| 7,206,627 B2 | 4/2007 | Abovitz et al. | |
| 7,452,357 B2 | 11/2008 | Vlegele et al. | |
| 8,104,480 B2 * | 1/2012 | Bodduluri .................. | 128/897 |

(Continued)

FOREIGN PATENT DOCUMENTS

| | | |
|---|---|---|
| CN | 102693352 | 9/2012 |
| EP | 0714642 | 6/1996 |

(Continued)

OTHER PUBLICATIONS

"ComputerWorld: Dispatches & Images from the Fringes of the Electronic Frontier", ComputerWorld. (Nexis abstract), Mar. 30, 1998.

(Continued)

*Primary Examiner* — Abolfazl Tabatabai
(74) *Attorney, Agent, or Firm* — Sharon Upham; Lena I. Vinitskaya

(57) ABSTRACT

Systems and methods for creating a treatment plan for cosmetic procedures, for example, a hair transplantation procedure, are provided. The treatment plan automatically modifies or generates one or more proposed harvesting or implantation sites within a first hair element based on one or more parameters in one or more second hair elements. Various techniques and methods described in the application provide for improved planning of a natural looking hair.

33 Claims, 10 Drawing Sheets

(56) References Cited

U.S. PATENT DOCUMENTS

| | | |
|---|---|---|
| 2002/0103500 A1 | 8/2002 | Gildenberg |
| 2004/0029068 A1 | 2/2004 | Sachdeva et al. |
| 2004/0034282 A1 | 2/2004 | Quaid, III |
| 2004/0197728 A1 | 10/2004 | Abolfathi et al. |
| 2004/0204760 A1 | 10/2004 | Fitz et al. |
| 2007/0078466 A1 | 4/2007 | Bodduluri et al. |
| 2007/0106306 A1 | 5/2007 | Bodduluri et al. |
| 2007/0150247 A1 | 6/2007 | Bodduluri |
| 2008/0004633 A1 | 1/2008 | Arata et al. |
| 2008/0122839 A1 | 5/2008 | Berglund et al. |
| 2011/0107270 A1 | 5/2011 | Wang et al. |
| 2011/0115790 A1 | 5/2011 | Yoo et al. |
| 2011/0251483 A1 | 10/2011 | Razzaque et al. |
| 2012/0158019 A1 | 6/2012 | Tenney et al. |
| 2012/0215231 A1 | 8/2012 | Wesley |
| 2012/0303384 A1 | 11/2012 | Stepaniak et al. |
| 2013/0058543 A1 | 3/2013 | Thomas et al. |
| 2013/0236074 A1 | 9/2013 | Hillebrand et al. |

FOREIGN PATENT DOCUMENTS

| | | |
|---|---|---|
| JP | H08-227454 | 9/1996 |
| JP | 2002-083318 | 3/2002 |
| WO | WO 98/21695 | 5/1998 |
| WO | WO 00/64379 | 11/2000 |
| WO | WO 2006/127142 | 11/2006 |
| WO | WO 2007/041014 | 4/2007 |
| WO | WO 2014/150459 | 9/2014 |

OTHER PUBLICATIONS

"Total Body Photography from Canfield", Imaging Systems and Software for Tracking Pigmented Lesions. Downloaded Nov. 22, 2013, (4 pages).

"Vectra m3 Sculpt the Dream", Brochure from Canfield Imaging Systems, Downloaded Nov. 22, 2013 (4 pages).

Alhaddab, Mohammed et al., "Effect of Graft Size, Angle, and Intergraft Distance on Dense Packing in Hair Transplant", Dermatol Surg. 31:6, Jun. 2005, 650-654.

Bernstein, Robert M. et al., "Follicular Transplantation", International Journal of Aesthetic and Restorative Surgery. vol. 3, No. 2., 1995, 119-132.

Bernstein, Robert M. et al., "The Logic of Follicular Unit Transplantation", Dermatologic Clinics vol. 17, No. 2, Apr. 1999, 277-296.

Bodduluri, R.M.C. et al., "Geometric Design and Fabrication of Developable Bezier and B-spline Surfaces", Transactions of the ASME vol. 116,, Dec. 1994, pp. 1042-1048.

Hoffman, Rolf et al., "Recent Findings with Computerized Methods for Scalp Hair Growth Measurements", The Journal of investigative dermatology symposium proceedings 2005, vol. 10, No. 3, 2005, pp. 285-288.

Jimenez, Francisco et al., "Distribution of Human Hair in Follicular Units—A Mathematical Model for Estimating the Donor Size in Follicular Unit Transplantation", Dermatol Surg. 25:4, Apr. 1999, 294-298.

Rassman, William R. et al., "Micrografting in Extensive Quantities", http://www.newhair.com/resources/mp-1995-micrografting.asp, (7 pages).

Riordan, Teresa , "Implanting Hair is Tedious, Exacting Work—the Perfect Work for a Robot", The New York Times Sep. 15, 2003, (1 page).

Shapiro, Ronald , "Principles and techniques used to create a natural hairline in surgical hair restoration", Facial Plast Surg Clin N Am 12 (2004), 2004, pp. 201-217.

PCT International Search Report and Written Opinion from the International Search Authority, for commonly assigned PCT/US2014/023318, Applicant: Restoration Robotics Forms PCT/ISA/210, 220 and 237 mailed Aug. 14, 2014 (18 pages).

English Translation of Office Action mailed Jul. 8, 2015 in connection with commonly assigned Taiwan Patent Application No. 103109329 Restoration Robotics, Inc. (4 pages).

* cited by examiner

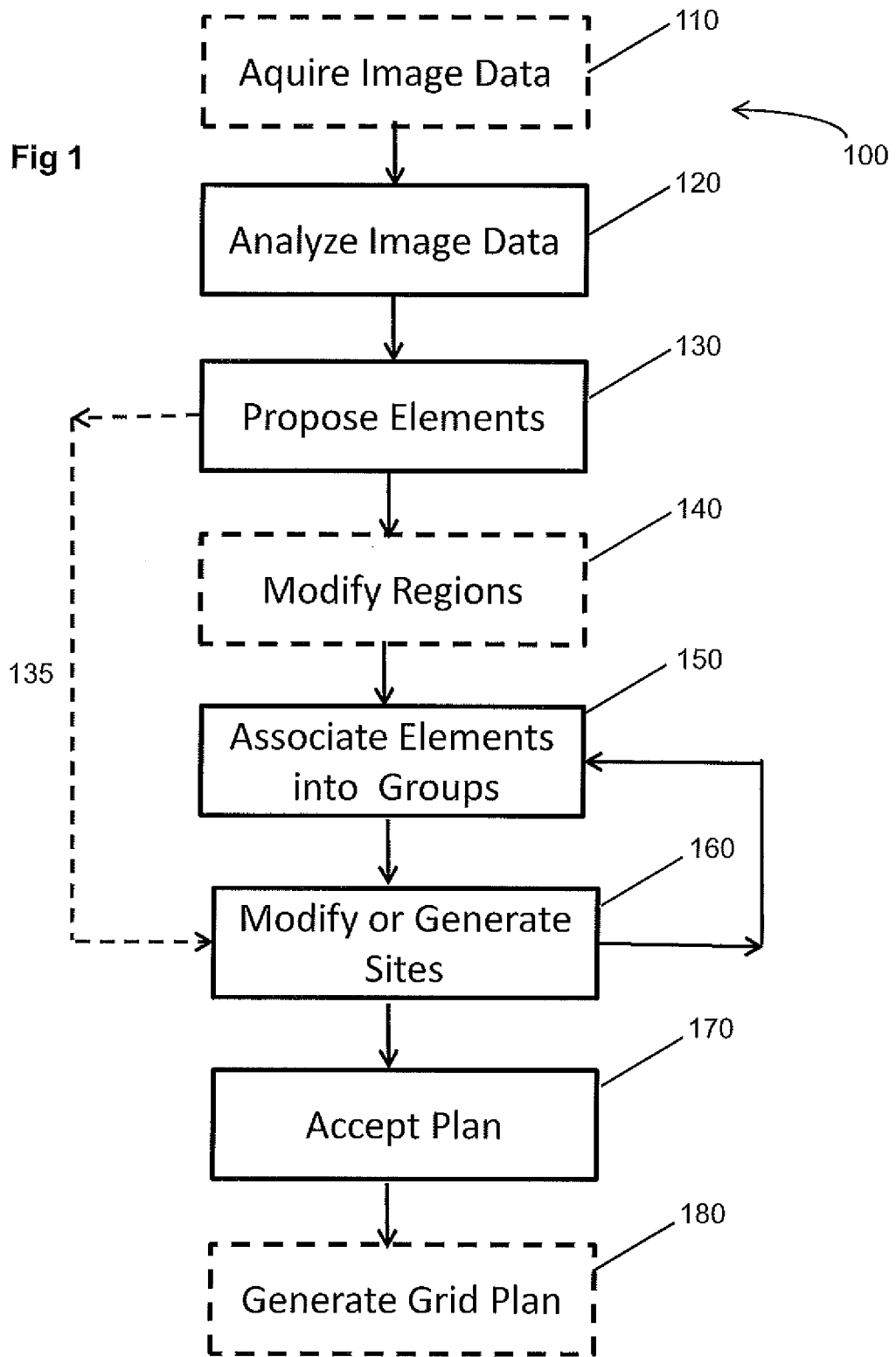

SYSTEMS AND METHODS FOR PLANNING HAIR TRANSPLANTATION

FIELD OF THE APPLICATION

This application relates generally to treatment planning systems, methods and method of their use. In particular, this application relates to hair transplantation planning systems i.e., harvesting and/or implantation of hair follicular units in a body surface, usually a scalp, and methods of their use.

BACKGROUND OF THE APPLICATION

Hair transplantation procedures are well-known, and typically involve (e.g., in a patient having male pattern baldness) harvesting donor hair grafts from the side and back fringe areas ("donor areas") of the patient's scalp, and implanting the harvested follicular units in a bald area ("recipient area"). Historically, the harvested grafts were relatively large (3-5 mm), although more recently, the donor grafts may be single follicular units, which are naturally occurring aggregates of 1-3 (and much less commonly, 4-5) closely spaced hair follicles that are distributed randomly over the surface of the scalp.

In one well-known hair transplantation process, a linear portion of the scalp is removed from a donor area using a scalpel cutting down into the fatty subcutaneous tissue. The strip is dissected (under a microscope) into component follicular units, which are then implanted into a recipient area in respective incisions or puncture holes made using a needle. Forceps may be used to grasp and place the individual follicular unit grafts into the needle puncture locations, although other instruments and methods are known for performing this task.

U.S. Pat. No. 6,585,746 discloses a hair transplantation system utilizing a robotic system, including a robotic arm and a hair follicle introducer associated with the robotic arm. An imaging system is used to produce a three-dimensional image of the patient's scalp, which is used to plan the locations to receive hair grafts. The entire disclosure of U.S. Pat. No. 6,585,746 is incorporated herein by reference.

No matter what type of hair transplant procedure is adopted, it is the aim of the physician to provide his patient with a natural looking head of hair. Currently physicians try and do this based on their experience based on procedures performed on prior patients, hoping that when they harvest hair from donor areas of the patient's head and implant it into recipient areas, they manage to do so in such a way that a natural looking head of hair results. However, it is not likely that a realistic image of what the patient might look like may be obtained based on prior experience with other patients. Everyone's hair is different, it is not of the same thickness, texture or density, and hair does not lie or fall in the same way on heads of different people. Moreover, not everyone's head shape or size is the same either, so there are many differences with respect to how the hair falls, and how it is parted too. Consequently, a result of a hair transplantation procedure performed on one patient does not necessarily look the same if the same procedure is performed on a second patient. Currently, it is only possible for one to look at the before and after photos of other people, and to guess what the outcome of a hair transplantation procedure might be.

Commonly assigned U.S. Pat. No. 7,806,121 and U.S. Pat. No. 8,104,480 (hereinafter collectively, "Bodduluri") illustrate systems and methods for planning transplantation of follicular units into a body surface of the patient. Both patents are incorporated by reference herein.

SUMMARY

A variety of systems and methods for planning various cosmetic and dermatological procedures, including hair transplantation, are provided in the present application. These procedures may be performed on the scalp, face and other skin and body surfaces.

According to one aspect of the present application, a method of planning for transplantation of follicular units in a body surface is provided. The method comprising: generating and displaying on a three-dimensional model of a body surface, at least two hair elements, each of the respective hair elements comprising one or more control points, the control points having corresponding parameters associated therewith; associating, with a use of a processor, a first and a second of the at least two hair elements with each other to form a hair group; generating or modifying at least one site within or on the first hair element, based at least in part on the parameters of at least one of the one or more control points of the second hair element. In some embodiments proposed follicular units sites are automatically modified, or generated and displayed based on the parameters of the control points of the hair group.

By the way of non-limiting examples, the hair element may be a hair patch or a boundary curve (e.g., hairline), the control points maybe located on a periphery or inside of the hair patch. The proposed sites may be hair harvesting sites, incision making sites, hair implantation sites, as well as various sites for placing and removing tattoos, or performing various cosmetic and dermatological procedures.

In some embodiments the parameter of the control point may be one or more of a location, an orientation or a density. In the case of density being the parameter, for example, in reference to hair transplantation and related procedures, the generation of the proposed sites may be based on an inverse transform algorithm between the proposed site and one or more control points. The density parameter may be weighed based on the distance of the associated control points from the proposed site.

In some embodiments, the method may further comprise projecting the 3-dimensional coordinates of a hair element into a 2-dimensional coordinate system and subsequently interpolating a procedure site (e.g., implantation site) in the 2-dimensional coordinate system. The interpolated implantation sites are then projected back into the 3-dimensional coordinate system, in which they are depicted on the 3-dimensional model of the patient. In some embodiments, the interpolation method may take into consideration density, and utilize a density parameter of a plurality of control points, wherein the plurality of control may comprise the one or more control points.

According to another aspect of the application, a method of planning for transplantation of follicular units in a body surface is provided, comprising: generating and displaying on a three-dimensional model of a body surface, a hair patch comprising a set of control points on the periphery thereof, the control points having corresponding parameters associated therewith; creating additional control points within the hair patch and/or on the periphery thereof; automatically generating and displaying a proposed follicular unit implantation site within or on the periphery of the hair patch based on the parameters of the control points and the additional control points.

According to another aspect of the current application, a system and a method of generating proposed procedure sites based on density interpolation is provided. The method comprising: projecting a location of a plurality of contour points of a body surface element in a three-dimensional coordinate system onto a two-dimensional plane; generating candidate procedure sites in the two-dimensional plane; determining an interpolated spacing value for each candidate procedure site, based on a density parameter of a plurality of control points associated with the body surface element; generating proposed procedure sites; projecting the two-dimensional location of the proposed procedure sites back to the three-dimensional coordinate system. In some embodiments, the method further comprises identifying candidate procedure sites that are not available as procedure sites due to the required spacing between the proposed procedure sites. In some embodiments, a formulation may be determined which associates density and spacing of the procedure sites. Additionally, the step of determining the interpolated spacing value may comprise utilizing the determined formulation.

According to another aspect of the application, a system for planning a transplantation procedure is provided, the system comprising: a user interface including a user input device, at least one non-transitory storage medium storing instructions, and a processor comprising one or more modules for executing operations on image data, the one or more modules comprising instructions for: generating and displaying on a three-dimensional model of a body surface, at least two hair elements, each of the respective hair elements comprising one or more control points, the one or more control points having corresponding parameters associated therewith; associating a first and a second of the at least two hair elements with each other to form a hair group; generating or modifying at least one site within or on the first hair element, based at least in part on the parameters of at least one of the one or more control points of the second hair element. In one embodiment the system further comprises an image repository. The system and method of the present application is especially useful when implemented on, or integrated with, an automated or computer-controlled system, for example, an image-guided robotic system comprising a robotic arm. The system may further include an imaging device to provide image data containing one or more images of the body surface and a tool for performing a procedure. The system may comprise an interface adapted to receive an image data containing images of a body surface, a processor programmed to perform various procedures and steps described in reference to various embodiments and methods of the present application, and a monitor configured to display a treatment plan as described herein.

In another aspect of the present application, systems and methods of planning for the transplantation of follicular units in a body surface is provided. Such systems and methods comprise generating and displaying a three-dimensional model of a body surface, selecting from an image repository a template, and generating and displaying one or more proposed hair elements based on the template. The step of generating may comprise generating a portion of the template. The portion may comprise a boundary curve or a hair patch.

According to another aspect of the present application, a system and method of planning for modification of a body surface (including facial features) is provided. Such systems and methods provide for associating various body surface elements into the groups and modifying certain features in a first body surface element based at least in part on one or more parameters of the control points from the second body surface element. In some embodiments modifications may be made automatically or with the user input. By way of non-limiting examples, the body surface elements may be a mole, freckle, wrinkle, scars, facial features such as eyes, nose, eyes, eyelids, lips, ears, chin, birthmarks, or facial defects.

Other and further objects and advantages of the invention will become apparent from the following detailed description when read in view of the accompanying figures.

BRIEF DESCRIPTION OF THE DRAWINGS

Features and advantages of the embodiments described herein will become appreciated as the same become better understood with reference to the specification, claims, and appended drawings wherein:

FIG. 1 is a flow chart illustrating an example of a general method for generating a treatment plan for use with a hair transplantation procedure.

DETAILED DESCRIPTION OF THE PREFERRED EMBODIMENTS

Figure 2A:
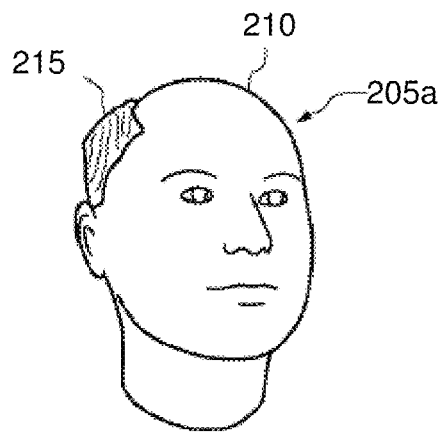
FIGS. 2a and 2b are images of a front and back view of a person's head.

In the following Detailed Description reference is made to the accompanying drawings that show by way of illustration specific embodiments in which the application may be practiced. In this regard, directional terms, such as "inner", "front", "away", "top", "right", "left", etc., are used with reference to the orientation of the Figure(s) being described. Because components or embodiments of the present application can be positioned in a number of different orientations, and the methods can be carried out in a number of different ways, the directional terminology is used for purposes of illustration and is in no way limiting. Also, the terms "coupled," or "attached," or "connected," or "mounted" as used herein, means directly or indirectly coupled, attached, connected, integrated, or mounted, for example, through one or more intervening components. It is to be understood that other embodiments may be utilized and structural or logical changes may be made without departing from the scope of the present application. The following Detailed Description, therefore, is not to be taken in a limiting sense, and the scope of the present application is defined by the appended claims.

When planning a hair transplantation procedure for a particular patient the physician has to take many parameters that vary from one patient to another into consideration. For example, hair density and the variation of density throughout different regions of the patient's scalp, the caliber of hair which may also vary throughout the patient's scalp, the manner in which the patient styles and/or combs his hair. Having taken these parameters into consideration, it is however not possible to know whether the hair that is implanted will match the already existing hair, give a natural-looking appearance, or look as if it has been transplanted. It is also not possible to know how the area from which hair is being harvested will look like after hair has been removed or harvested.

Natural looking randomness is important not only for the critical hairline element but in the balance of the recipient sites, and the donor site too. To this end, each hair element, comprising, for example, hairlines, hair patches and the donor area should not be designed or planned independent from each other. In planning a hair transplant, the physician has to ensure that his plan offers the best outcome based upon the existing hair that exists on the patient's head, for example, the density or the distribution of existing hair, its spacing, angles, how the patient generally parts and/or combs his hair, or whatever else contributes to making the hair transplant look natural. One aspect of the current application enables such a natural looking randomness to be maintained, for example, throughout the patient's scalp. In addition, another feature of the current application enables a physician to obtain an image of what his/her patient may look like at various stages during, as well as, after a hair transplantation procedure is completed, based upon an image of their head, and their actual hair. Utilization of various aspects of the current application provides not only an image of what the newly implanted hair may look like, but of what the areas from which the donated hair will look like once the hair has been harvested from the donor element(s). According to another aspect of the current application a means is also provided by which a physician is able to propose potential visual appearances and aesthetic outcomes to a patient, explaining the various functional and/or aesthetic advantages and disadvantages of the potential treatment plans, along with a discussion of the time and/or cost associated with each proposed treatment plan. In this manner the patient is able to see what he/she may look like in each of the scenarios discussed, which reduces the chances of a patient misunderstanding what the physician may be trying to convey to a patient. In yet a further aspect of the current application a means is also provided by which the physician is able to plan one or more sessions of transplant surgery, optimizing the process to potentially reduce the number of sessions required to complete a hair transplant. This application provides the physician with a tool to enable him or her to ensure that there is, for example, sufficient hair in the donor areas, and hair of the correct type and caliber to provide the look that the patient is hoping for. If there is not, the current application provide the physician with a tool to enable him/her to illustrate to the patient what possible hair transplantation options are available to him or her based on the number, type, and caliber of hair they have available in the donor areas.

The system and methods described in the present application also provide the physician with a means for planning the hair transplantation process, the number of sessions etc.

It should be noted that although the application is particularly useful in hair harvesting and implantation, it is not limited to hair transplantation. The application may also be beneficial to other procedures that require a model of the patient's body surface and parts, including, facial and head features, for example, various cosmetic and dermatological procedures involving treatment planning (e.g., plastic surgery, wrinkle removal or reduction, injections of cosmetic substances, skin grafting procedures, correction or removal of birth mark defects, facial reconstruction, rhinoplasty, contouring of the eyes or lips, remodeling of ears, nose, eye-lids or chins, facial rejuvenation, laser skin resurfacing, skin tightening, etc.) may benefit from the system and method of the applications described herein. One example of applicability of the application is in diagnostic skin imaging for cosmetic or other medical purposes, for example skin grafting or tattoo removal. For convenience of description, the following description will be discussed by example in reference to hair transplantation procedures. It should be noted, however, that such description is for the purposes of illustration and example only and is not intended to be exhaustive or limiting.

In accordance with one embodiment of the application, a treatment plan for a hair transplantation procedure may be created at least partially by a computer. The treatment plan automatically modifies, or generates one or more proposed follicular unit sites within a first hair element based on one or more parameters of hair follicles or follicular units in one or more second hair elements. In other embodiment of the application, the treatment plan automatically modifies, or generates proposed follicular unit sites within a first hair element based on one or more parameters of follicular units in the hair group, the hair group comprising a first and one or more second hair elements. In either case, the parameter information between two hair regions is shared, thus providing a tool to facilitate a more natural looking hair transplantation result. The treatment plan may take into consideration one or more parameters, including, but not limited to: a location of one or more hair elements, the geometric profile of hair elements, the number and/or type of follicular units to be harvested/implanted, a degree of randomness associated with particular harvest/implant locations, spacing between adjacent implant locations, depth of follicle, depth of implant, orientation of follicles or follicular units, patient identification (for example hair color, ethnic origin, age etc.), marker location(s), and/or the density of harvest/implant sites. In some embodiments, information about a particular follicular unit or combination of follicular units can be obtained from a database of follicular units. This database may contain information specific to the patient in question or to patients in general. The database may contain information categorized by ethnic origin, gender, and/or age, for example. In yet a further embodiment, the treatment plan may be generated or modified based on control points on or within the first and/or second hair elements. The control points can be individual points, lines, shapes, or other markers that can be used to provide a basis for the generation or modification of follicular unit sites within the first hair element.

After the treatment plan has been created at least partially by the computer, the user can accept or alter the treatment plan. Once the treatment plan meets the expectation of the physician, user and/or the patient, the user may register the treatment plan with a patient. In some embodiments, this may be accomplished by using one or more cameras to identify one or more markers that could be positioned directly on the patient or on a device used on the patient. The marker may be a reflector that is secured to the patient, an ink mark drawn on the patient, or an anatomy of the patient. Alternatively the marker may be, for example, a marking on a skin tensioning device that may be utilized by the physician in the hair transplantation procedure. The identified marker(s) may be used to determine a position and/or orientation of an element on the patient.

Hair transplantation procedures that are carried out using automated (including robotic) systems or computer-controlled systems have been described, for example, in U.S. Pat. No. 7,962,192, commonly owned by the assignee of the present application, which is incorporated herein by reference. After the robotic system has been initiated and calibrated, image data of the body surface is acquired and processed by the system computer to identify objects, in particular follicular units in a donor element, for example, on a human scalp. From images of this element of interest, image segmentation and screening software residing in the computer identifies and selects particular follicular units of interest for harvesting from the scalp.

In accordance with various embodiments of the application, a system for planning a procedure for transplantation of follicular units in a body surface (e.g., a scalp) of a patient may comprise a user interface, processor (e.g., software-controlled), a monitor, and at least one input device. These components are common to virtually all modern computer systems, whether a stand alone (e.g., "personal") computer system, or in a system employing a centralized server with multiple remote terminal(s). It will be appreciated that embodiments of the planning system are preferably (if not exclusively from a practical point of view) software implemented, and may be run on any computer system having the basic components (processor, monitor, input device), so long as such computer system is equipped with sufficient available memory and an appropriate graphic generation and display capability. The computing system may include one or more processing units, one or more non-transitory storage media (which may take the form of, but is not limited to, a magnetic storage medium; optical storage medium; magneto-optical storage medium; read only memory; random access memory; erasable programmable memory; flash memory; and so on), and/or one or more input and/or output components for transmitting output to and/or receiving input from one or more other components (such as one or more displays, keyboards, mice, track pads, track balls, styluses, printers, speakers, cameras, video cameras, and so on). The processing unit may comprise one or more modules to execute instructions stored in the storage medium in order to perform one or more computing device functions, such as one or more treatment planning methods. The system or the processing unit may additionally include an image repository, the image repository comprising templates, images of one or more patients and/or images of portions of templates or patients. The system can be configured to implement all the methodologies, processes and techniques described herein.

Although it may be suggested that the computing system include particular components arranged in a particular configuration, it is understood that this is for the purposes of example. In various implementations, the computing system may include any number of computing system components (such as one or more busses, displays, networking components, dedicated image processors, co-processors, memories, hard drives, ports, graphics adapters, and so on) arranged in different configurations without departing from the scope of the present disclosure. For example, in one or more implementations the computing system may include multiple cameras and/or video cameras arranged to capture images and/or video of the same scene. By way of another example, in various implementations the computing system may include one or more interfaces for controlling machinery such as automated and/or computer-assisted surgical machinery.

It will also be appreciated that embodiments of the application may be implemented over the internet, e.g., with a user of such system employing his or her home computer as at least a part of the user interface (monitor and input device) that interacts with a remote server or computer. In such an internet-based planning system, the software that implements and controls the user interface may reside in whole or part on the user's computer or on the remote server/computer, preferably transparent to the user. In one such embodiment, the remote server downloads one or more software modules to the user's computer for temporary or permanent use.

Exemplary embodiments of a software implemented and controlled user interface for planning a follicular unit transplantation procedure will now be described in conjunction with the accompanying figures. It will be appreciated that various and multiple variations of the described embodiments may be implemented without departing from the general scope of the application, which is set forth in the appended claims.

FIG. 1 is a block diagram illustrating an example of a general methodology of a treatment planning procedure according to the present disclosure. As a preliminary matter, at step 110, image data is acquired, for example, by using an image acquisition or imaging device, or from pre-existing data stored in the computer system's memory, or any other technique known in the art. For example, in some embodiments, the image data can be retrieved from the patient's electronic records or general patient data. In other embodiments, the image data can be created real-time, using a digital camera.

In step 120, a processor or an image processor, processes and records information associated with the image data. Such information comprising, for example, the location and orientation of existing follicular units or hair follicles, information pertaining to scars, moles, freckles, wrinkles, facial features, tattoos or any other such body surface features.

In step 130, based on the information determined at step 120, the processor proposes hair elements, or body surface elements, including facial elements (and consisting of the proposed modification of existing body surface features) and one or more presentation components in the treatment planning system, such as a monitor, are used to visually present information indicative of the proposed hair elements/body surface elements. In reference to hair transplantation, the proposed hair elements may comprise, for example, a hairline or a hair patch. The proposed hair elements may comprise elements from which follicular units are to be harvested from or implanted into. In one embodiment, the proposed hair elements comprise a proposed boundary curve and/or proposed harvesting/implantation sites. In some embodiments, the proposed hair elements are proposed based on the image data alone. In other embodiments the hair elements are proposed based additionally on templates residing in the image repositories of the computer system. These templates may be automatically selected by the computer system based on the image data processed, or alternatively they may be selected by the user, or by a combination of both. In some embodiments once a template has been selected, portions of the template may further be selected.

Optionally in step 140, executable instructions may be provided to enable the user to modify the proposed hair elements/body surface elements by modifying the proposed boundary curve and/or the proposed harvesting/implanting sites based upon their analysis of the displayed image. The proposed boundary curve and/or the proposed harvesting/implanting sites may comprise control points to assist in the modification process.

In step 150, two or more hair elements/body surface elements are associated to form a group, such as hair group. Sites are modified or generated in step 160 based on the defined hair groups. Take, for example, a hair group comprising two hair elements. In one example, one or more proposed follicular unit sites in a first hair element may be now modified or generated based on one or more parameters of follicular units in the second hair element that is in the same hair group with the first element. In another example, one or more proposed follicular unit sites in a first hair element are modified or generated based on one or more parameters of follicular units in the hair group as a whole.

In the event that the user wishes to associate a different combination of hair elements to modify or generate more proposed sites, steps 150 and 160 may be repeated until all desired combinations have been associated and the desired proposed sites modified or generated.

In step 170, the treatment plan is accepted and, optionally, in step 180 a grid plan (described in more detail below) may be generated.

Although the method 100 is illustrated and described as including specific operations performed in a specific order, it is understood that this is for purposes of example. In various implementations, some operations may be performed in another order without departing from the scope of the present disclosure. In other implementations, only a subset of the various operations may be required, again without departing from the scope of the present application.

At any stage of the procedure, the proposed plan may be saved for further modification, editing or updating at a later date. This may be beneficial if after execution of a particular session of the treatment plan, the patient's hair does not grow as predicted, requiring modification of the treatment plan. Or, after execution of a particular session of the treatment plan, the patient has a change of mind, or cannot afford to have the entire procedure performed as planned, requiring modification to address his financial concerns, while at the same time providing him with a hair transplant that has a natural looking appearance.

Figure 2B:
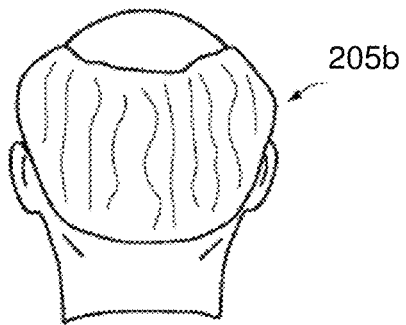

FIGS. 2a and 2b, illustrate an example of an embodiment of how image data is acquired (step 110). Images 205a and 205b are acquired of a body surface of a patient, for example, various views of the patient's head (and, in particular, scalp), for which the subject transplantation procedure is being planned. By way of non-limiting example, the images may be acquired using a hand held digital camera, or even a mobile telephone camera, and input through the user interface of the planning system, in accordance with well-known and available technology for transmitting digital image data. It is not necessary to include images of every portion of the patient's head, since it is known to those skilled in the art that modeling software can generate a sufficiently accurate three-dimensional surface model of the head/scalp from just a few views, for example, from four (4) to six (6) views from different directions and sides, including, for example, from the top. Dependent on the purpose of the treatment plan (e.g., facial cosmetic procedure, or planning hair transplantation on the scalp), the minimum number and angles/directions of the desired views may be adjusted to achieve sufficiently accurate model. The acquired images are then processed to generate a three-dimensional model of the patient's head (e.g., scalp) using modeling software. It will be appreciated that any suitable software program may be used.

In an alternate embodiment in which acquired images of the patient's head/scalp (or other applicable body surface) are not provided, the modeling software is configured to generate (by selecting menu option "generate") a three-dimensional model based on inputs relating to selected characteristics, such as ethnic origin or race, and/or other characteristics selected through one or more menus, some objective (e.g., gender, age) and others purely subjective (e.g., attractive, symmetrical features, long forehead).

In some embodiments, further input information is provided to the planning system in addition to generating the body surface model. For example, particular features specific to hair follicles (e.g., color or coarseness) may be derived from the images and/or input through the user interface. Further information may be either user input or determined from the acquired images using image processing, such as geometric shape of the body surface (e.g., patient's head), existing hairlines, the existence of scars or moles, the location of where follicles have previously been harvested from or implanted into, and a number of each type (i.e., single or multiple follicle) and color (e.g., dark, light, gray, etc.) of follicular unit that are available for harvesting. It will be appreciated that the three dimensional model can alternatively be generated by a number of other methods, for example, using a 3D laser scanner and/or by stitching multiple digital images together. The system of embodiments of the present application will use the three dimensional information in the same way, without regard to how it is generated.

Whether from the acquired images, or through other descriptive feature inputs, the modeling software generates and displays on the user interface monitor of the planning system a three-dimensional model of the patient's head/scalp. With reference to hair transplantation, this model will represent the patient's head/scalp, and therefore will typically exhibit characteristic of male/female baldness patterns, comprising of bald regions 210, follicular unit populated regions 215 and, and/or regions which are more or less densely populated than others. The populated regions 215 will comprise follicular units which are grouped to form regions of hair which border less populated regions, or bald regions. These regions of hair may have geometry associated with them. The follicular units have various parameters such as type, caliber, orientation with respect to the scalp, spacing between adjacent follicular units, height of follicles above the scalp, for example.

Figure 3:
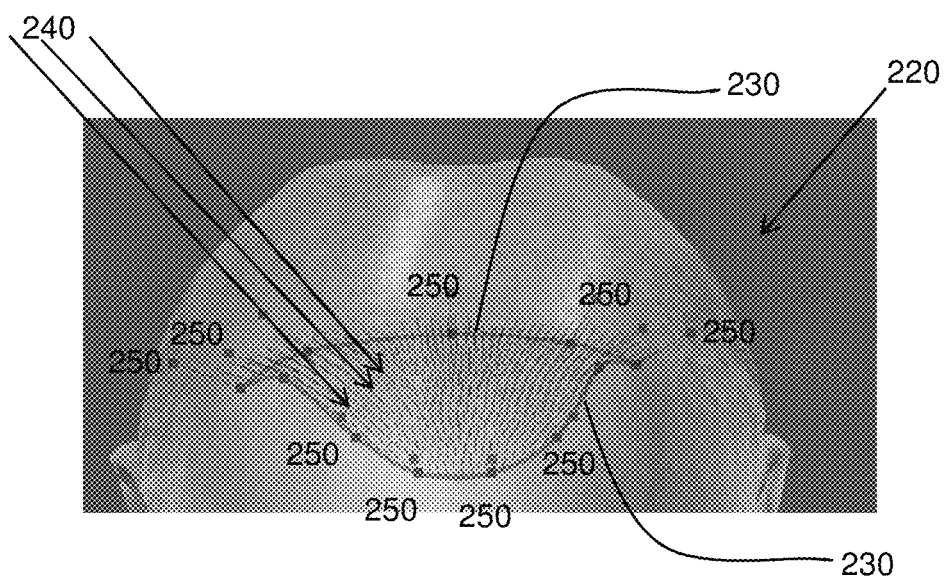
FIG. 3 depicts an example of a proposed hair implantation element according to one embodiment of the application.

Based on these characteristics, information, and/or one or more physical features determined from processing the acquired images, the modeling software automatically generates and the planning system displays on the user interface monitor of the planning system, a visual representation of one or more proposed elements 220 for follicular units sites as shown in FIG. 3 (step 130 of the flow chart of FIG. 1). According to one aspect of the present disclosure, the planning system may automatically propose a treatment plan. For example, hair elements may be proposed into which hair follicles may be implanted to create a natural look for the patient. This may be accomplished by mapping anatomical elements determined from the acquired imaged superimposing the proposed hair elements, and displaying them on the user interface monitor. Such anatomical elements comprising, for example, the geometric shape of the hair populated regions and the geometric shape of the bald regions, follicular unit populated regions, the location of the eyes, ears and nose of the patient. One or more proposed elements for follicular unit sites may, for example, as illustrated in FIG. 3 be proposed in a bald region 210 and comprise a boundary curve 230 and optionally one or more proposed implantation sites 240. In this particular illustration control points 250 are illustrated. These control points 250 may be generated by computer system and/or determined by the user. Typically the control points lie on the boundary curve, though they may reside within the hair element 220 or adjacent thereto. The user may optionally modify the boundary curve 230 by using a conventional click and drag motion of a computer mouse (step 140) to drag the boundary curve 230, or drag the control points 250. The system is configured such that the operation of dragging the control points 250 is interpolated to every point along the boundary curve 230 between adjacent control points.

According to some embodiments, a treatment plan may be generated based at least in part on imaging data such as images from one or more image repositories. For example, the planning system may map anatomical elements determined from the acquired images to model heads or templates that are within the image repositories to automatically propose a treatment plan. In some embodiments, the user may select an image or template from patient information repositories containing images from one or more patients. For example, the template may identify the final outcome or the subsequent stage that the patient wishes to reach in terms of his/her hair transplantation treatment process. These templates may, for example suggest different hair style outcomes that may be achievable. These templates may comprise templates for men, women, boys, or girls; templates corresponding to various ethnic origins; templates corresponding to various head shapes; and/or templates corresponding to various degrees of hair loss, such as a template based on the Norwood scale of hair loss. For example, a template exhibiting a male Caucasian patient with hair receding mildly in a wedge-shaped pattern may be used for a patient with similar wedge-shaped pattern of baldness. Having selected the most appropriate template or combination of templates, the modeling software generates and the planning system displays on the user interface monitor of the planning system, a three-dimensional model of a patient's head/scalp, adding in or superimposing one or more elements as dictated by the selected template using, for example, a best-fit algorithm. That is, a visual representation of the patients existing hair regions, including hair elements into which it is desired that follicular units be implanted. These representations are generated such that they are scaled to fit on the three dimensional model of the patient's head/scalp. Optionally, the representations may be modified in shape and size to fit the three dimensional model of the patient's head/scalp.

Figure 4:
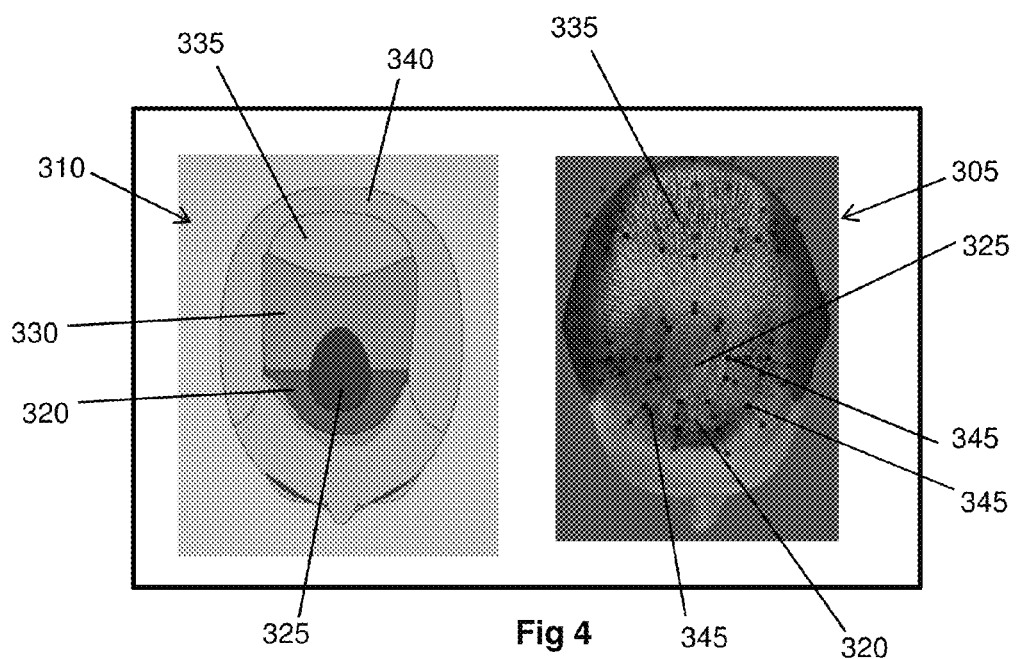
FIGS. 4 and 5 are examples of the representative monitor views generated as part of a treatment planning illustrating the use of two different templates.

In another implementation, the images from the repositories can be used to identify regions of interest through segmentation, contouring, or the like. For example, images from the image repositories may identify hair elements which are proposed to be added to the three-dimensional model of a patient's head/scalp. For example, the user may select a predetermined hair harvesting/implantation element from a range of possible options. This is illustrated in FIG. 4 which shows a view on a user interface monitor of the planning system, on which a three dimensional model 305 of the patient's head/scalp is displayed on the right hand side (as viewed by the reader). On the left, a template 310 is illustrated, the template comprising several selectable elements into which it may be proposed that follicular units be implanted. In this particular example, the user may select one or more of a frontal element 320, a forelock element 325, a mid-scalp element 330, or a crown element 335 as element(s) into which hair is to be implanted. The donor area 340 (shown on the left template side) is not a selectable element, this being the element from which follicular units will be harvested to fulfill the implantation requirement. Having selected the desired elements into which follicular units are to be implanted, the modeling software generates and the planning system displays on the user interface monitor of the planning system representations of the selected elements on the three dimensional model 305 of the patient's head/scalp. In the illustrated example, on the image appearing on the right-hand side of the user interface monitor, outlines of proposed hair elements comprising control points on the periphery thereof can be seen, indicating that the frontal element 320, the forelock element 325 and the crown element 335 have been selected by the user. In this particular example, representations are generated such that they are scaled to fit on the three dimensional model of the patient's head/scalp. As shown on the right hand side of FIG. 4, the representations may comprise control points 345 which can be selected and dragged, thus enabling the user to modify the shape and sized of the representations on the three dimensional model of the patient's head/scalp.

Figure 5:
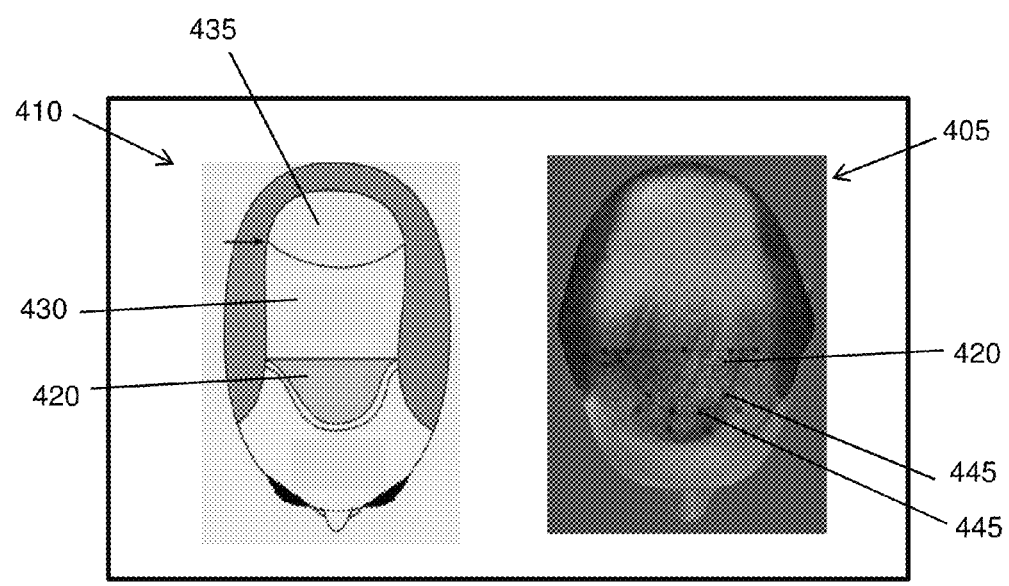

FIG. 5 illustrates another example in which once again a three dimensional model 405 of the patient's head/scalp is displayed on the right hand side (as viewed by the reader), and a template 410 on the left illustrating one fewer elements than that illustrated in FIG. 4. In this example the user may only select from a template 410 one or more of a frontal element 420, a mid-scalp element, 430 or a crown element 435 as element(s) into which hair is to be implanted. This limitation of elements available for selection may be due to a prior choice of the user (for example, the user having selected this template from a selection of templates), the session of the hair transplantation procedure (for example the first session of three transplantation sessions), the limited number of donor follicular units, financial reasons, the physician's choice, or based on prior transplantation data etc. In this instance, if the user has selected that hair to be transplanted only into the frontal element, then the modeling software generates and the planning system displays on the user interface monitor of the planning system a representation of the frontal implant element 420 on the three dimensional model 405 of the patient's head/scalp. As illustrated, the representation comprises control points 445 which can be selected and dragged, thus enabling the user to modify the shape and sized of the representations on the three dimensional model 405 of the patient's head/scalp.

According to yet another aspect of the application, having selected from a range of possible templates a template which best identifies his/her patient, the modeling software generates and planning system displays on the user interface monitor of the planning system, a selection of treatment plan options. These treatment plan options may, for example, include a high density follicular unit implantation in the frontal element only, a lower density follicular unit implantation in the frontal element only, follicular unit implantation in the frontal and mid-scalp elements, or perhaps follicular unit implantation throughout the scalp of the patient, for example. It will be apparent to the reader that the number of options available is numerous and as such all examples are not described herein. In another embodiment, the modeling software may additionally provide an indication of which of the many options are actually available to the patient, for example by making it impossible to select certain options. For example, if an option of a high density follicular unit implantation throughout the patient's scalp is not possible due to the lack of donor follicular units that can be harvested, for example, the modeling software will not enable that specific treatment option, and will not make it an option that can be selected by the user. To implement this option, it will be apparent that the computer system will have had to attain information pertaining to the number of, and optionally the type, of follicular units available for implantation. This information may be input by the user into the treatment planning system, or be provided by the treatment planning system itself, in analyzing the image data, and determining how many follicular units are available for harvesting without detriment to the aesthetic appearance of the hair in a donor area on the patient's head. In an alternative configuration, the treatment planning system may be configured to plan the harvesting of follicular units from the existing follicular units, and based on the number and/or type of follicular units proposed to be harvested, can utilize this number and/or type in generating a proposed implantation plan. It will be apparent to the reader that the options that are enabled to be selected by the user will vary based on context.

However generated, the modeling software generates and the planning system may display on the user interface at least one proposed hair element, for example a particular hair implantation site. Having selected the hair elements within which, for example, follicular unit implantation is desired, the treatment plan may be further customized.

According to another aspect, the present application also provides a treatment plan which automatically modifies, or generates proposed follicular unit sites within a first hair element based on one or more parameters of follicular units in one or more second hair elements. This aspect of the application will now be described with reference to FIGS. 4 and 6a. It was explained above (in relation to FIG. 4) that the user had selected hair implantation elements 320, 325 and 335. Let us assume that the three dimensional model of the patient's head/scalp 305 as displayed on the right hand side (as viewed by the reader) represents the current state of the patient's head. A state in which the frontal and forelock element are more densely populated with hair than the crown element. The user may select, for example, a first element, the crown element 335, as an element which the user would like hair grafts to be implanted into, the implantation carried out such that the resulting density of follicular unit implants provides for a density substantially equivalent to that of the forelock element 325. The user therefore desires that a treatment plan be provided such that the follicular unit implantation sites within the first element, the crown element 335, are generated based on a parameter (for example the density) of the follicular units in a second element, the forelock element 325.

Figure 6A:
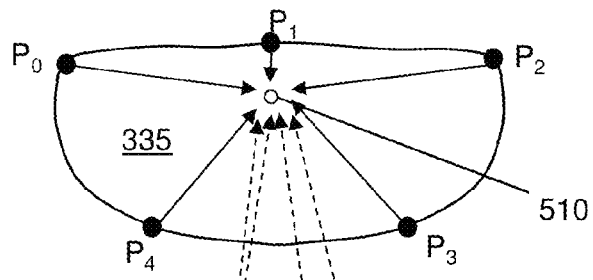
FIG. 6a depicts an example of how control points over two hair elements may influence a proposed site.

This scenario is depicted in greater detail in FIG. 6a. It should be apparent to the reader that although the shape and details of the various elements have been simplified, the regions depicted as 325 and 335 in FIG. 4 generally correspond to the regions depicted as 325 and 335 in FIG. 6a. The first of the elements 335 comprises a set of one or more control points that are associated with it, illustrated by the five control points, $P_0$, $P_1$, $P_2$, $P_3$ and $P_4$. The second element 325 also comprises a set of one or more control points that are associated with it, illustrated by the four control points $Q_0$, $Q_1$, $Q_2$, and $Q_3$. These control points may be determined or proposed by the treatment planning system. Alternatively they may be indicated as control points by the user by simply moving a cursor on the screen to the location of the proposed control point, and clicking a button on a mouse to create a control point. In another alternative, control points proposed by the treatment planning system may be modified by the user, once again using the drag feature and a mouse for example, or additional control points may be added to those proposed by the system. The control points may be based on elements within the image of the patient's body surface, such as follicular units or hair follicles, or be based on input provided by the user, virtual. The properties or parameters associated with any control point may be determined from the image data, provided by the treatment planning system, or provided by the user. These parameters, in reference to hair, may include, for example, information on the follicular unit type, the length of hair follicles, the angle of hair follicles or a density value associated with a hair follicle or follicular unit (typically based on determining the number of hairs within a specified distance of the control point). With reference to cosmetic or dermatologic treatments, these parameters may comprise skin coloration, skin texture, skin tautness, facial feature dimensions, facial topology etc. Once created, in this aspect of the application, rather than the parameter(s) of the proposed implantation site 510 being based on only the five control points $P_0$, $P_1$, $P_2$, $P_3$ and $P_4$ which surround it, as depicted by the solid arrows, the parameter(s) of the proposed implantation site 510 are based on all nine control points $Q_0$, $Q_1$, $Q_2$, $Q_3$, $P_0$, $P_1$, $P_2$, $P_3$ and $P_4$, as depicted by the solid and dashed arrows. The parameter(s) of the proposed implantation site 510 may be interpolated from the parameter(s) of the nine control points.

It will be appreciated that there are numerous methods of interpolation that may be utilized for this application. One example of an interpolation technique is one in which the proposed hair site parameter is based on an inverse distance transform algorithm. This method of interpolation calculates the distance between the point to be interpolated (e.g., 510) and each of the respective control points, $Q_0$, $Q_1$, $Q_2$, $Q_3$, $P_0$, $P_1$, $P_2$, $P_3$ and $P_4$, and applies a weighting to each of them based on the distance from the point to be interpolated (510). In this manner, the control $P_1$ will have a greater influence on the interpolated value than the control points $P_0$ and $P_2$. Similarly control points $Q_2$ and $Q_3$ will have the least influence on the value of the interpolated point 510. For this algorithm, each of the control points may be utilized and provide a contribution to the determined value of the point 510 to be interpolated. In an alternative, only those within a certain distance from the point to be interpolated may be considered or, for example, only the two closest points. The interpolated value applied to the point to be interpolated 510 may be based on a linear interpolation of the control points, a polynomial interpolation, spline interpolation, non-linear interpolation (such as a Gaussian process), or other forms of interpolation that will be known to those skilled in the art. The type of interpolation utilized will generate varying results, and some will utilize more time in the generation process.

Figure 6B:
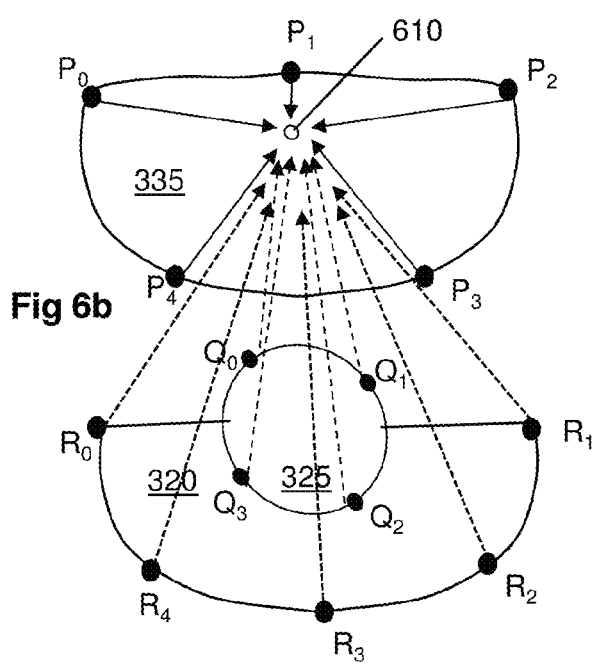
FIG. 6b depicts an example of how control points over three hair elements may influence a proposed site.

Another embodiment will now be described with reference to FIGS. 5 and 6b. In this example, the user additionally selects the frontal element 320. Therefore, the treatment plan is generated such that the follicular unit implantation sites within the first element, the crown element 335, are generated based on a parameter (for example the density) of the follicular units in more than one second element, in this case two elements: the forelock element 325 and the frontal element 320. In this particular situation, the parameters of the proposed implantation site 610 are based on all fourteen control points $Q_0$, $Q_1$, $Q_2$, $Q_3$, $P_0$, $P_1$, $P_2$, $P_3$, $P_4$, $R_0$, $R_1$, $R_2$, $R_3$ and $R_4$ as depicted by the solid, dashed and dotted arrows (the frontal element 320 has 5 additional control points $R_0$, $R_1$, $R_2$, $R_3$ and $R_4$.) The parameter(s) of the proposed implantation site 610 may be interpolated from the parameter(s) of the fourteen (14) control points, or a subset thereof.

In the examples indicated above, it can be seen that the referenced control points were all disposed on the periphery of the hair elements, that is, they were contour control points.

Figure 7:
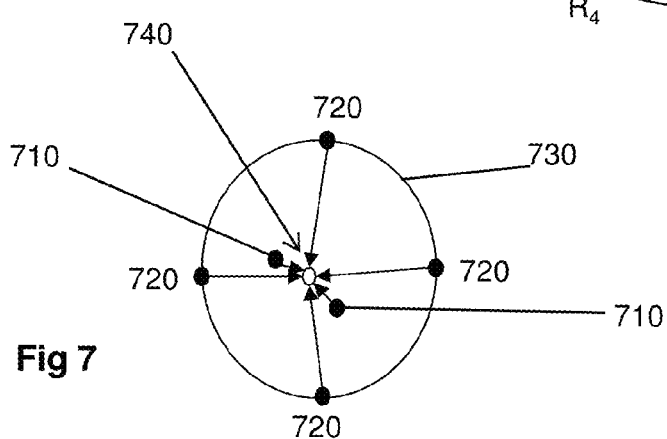
FIG. 7 depicts an example of how hair swirls may be generated.

To further customize the treatment planning process however, the system may also add specific control points 710 other than contour control points 720 to produce specific effects, such as an implant angle or density, or to achieve hair swirl and parting. Individual control points 710 may be placed inside the boundary curve 730 by the user, as shown in FIG. 7 (the two black circles 710 within the boundary curve 730). Any interpolated value of the implantation site 740 will be affected by both contour control points 720 and the individual control points 710, as illustrated in FIG. 7. This additional customization may be utilized on a single hair element or in combination with the techniques described above.

Implementation of the selection of hair elements may be provided by a listing of the elements and an associated check box for each element on the monitor. By checking each of the desired hair elements that the user desires to be associated with one another, these hair elements can be grouped together, in addition to any control points associated therewith. Thus proposed sites may be influenced by all associated elements and their associated control points.

Figure 8:
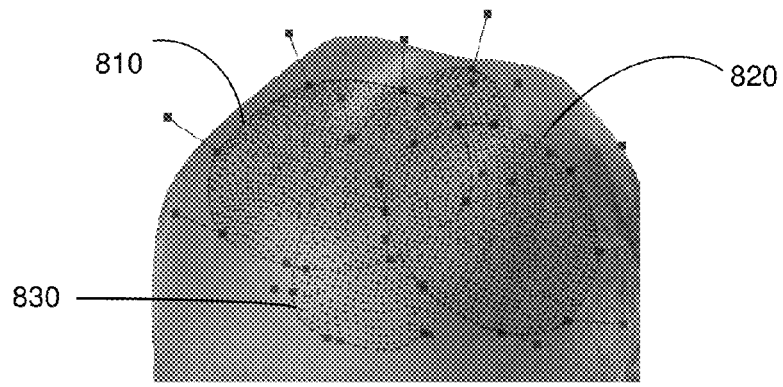
FIG. 8 illustrates by example a person's head on which three overlapping hair elements are superimposed.
Figure 9A:
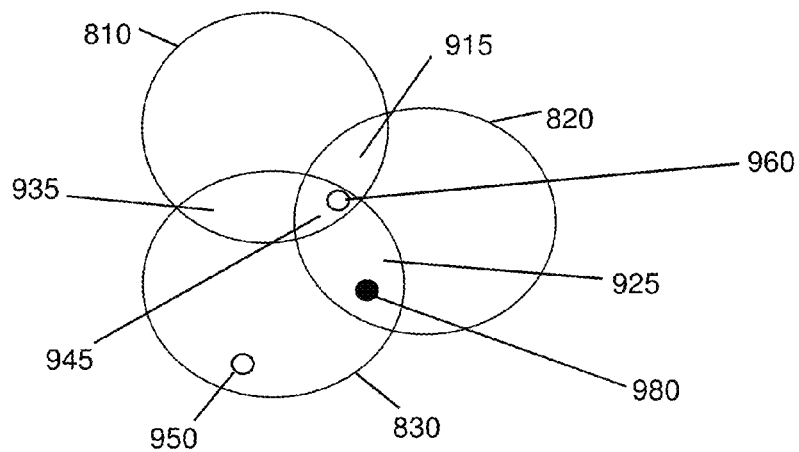
FIGS. 9a and 9b depict the three overlapping proposed hair elements of FIG. 8.
Figure 9B:
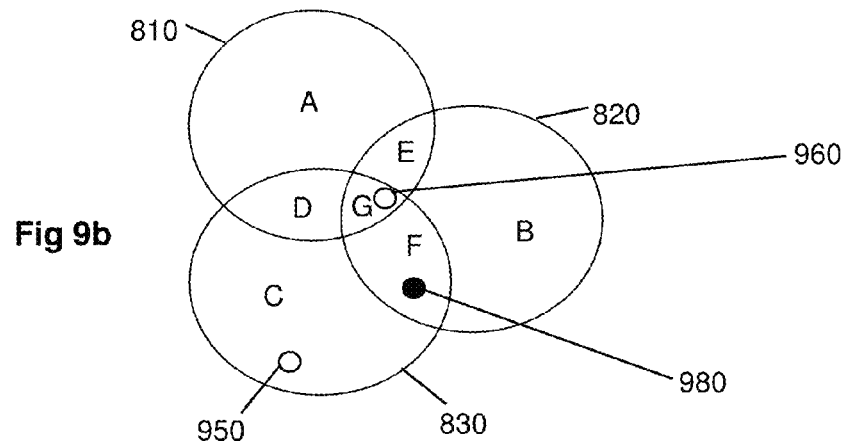

When multiple hair elements are placed on the same body surface, it is possible that they may at least partially overlap each other. This is illustrated in FIG. 8, which shows an image of a scalp of patient, on which three hair elements have been identified, for example, proposed hair patches 810, 820 and 830. These elements may have been identified by the treatment planning system, the user, or a combination of both. Such overlapping elements may be generated, for example, when the user is trying to plan implantation elements which are customized to the patient, taking into account existing hair elements which already have hair, avoiding elements where hair has already been implanted, or avoiding elements in which implantation is not viable (due to pre-existing medical conditions, scars, or other such reasons) for example. These combinations of elements represent shapes that are not necessarily provided in the form of templates by the treatment planning system. However, an overlapped element may result in the generation, for example, of proposed implantation sites that have incorrect interpolated values. For ease of explanation the hair elements identified in FIG. 8, they have been schematically replicated in FIGS. 9a and 9b. FIGS. 9a and 9b illustrate three hair elements 810, 820 and 830, which may, for example, have been generated such that they fill a bald area of a patient's scalp, the elements around it having already existing hair. As more clearly illustrated in FIG. 9a, these three hair elements overlap each other to varying degrees. Hair elements 810 and 820 overlap or intersect in the area denoted 915; hair elements 820 and 830 overlap or intersect in the area 925; and hair elements 830 and 810 overlap or intersect in the area 935. Finally, all three hair elements 810, 820 and 830 overlap or intersect in area 945.

Let us assume that the user were to indicate that the proposed implantation sites in the hair element 820 were to be based on the parameters of control points on the contour of, and within, the hair elements 820 and 830. Based on the explanation given above, when a proposed implantation site 960 is generated using interpolation techniques, the interpolation technique will take into consideration the parameters of control points on the contours of hair elements 820 and 830, and of control points within those elements, such as the control point 980, as illustrated. However, control point 980 falls within both elements 820 and 830, and as such will be considered twice when the interpolated value of the proposed implantation site 960 is determined. It will be considered once when the values of control points on the contour and in element 820 are considered, and again when the values of control points on the contour and in element 830 are considered. If the parameter value generated were, for example, density, it will be apparent that the interpolated value of the proposed implantation site will therefore be incorrect (potentially with the density being twice as high), because the control point 980 will have been considered twice. For the case of the user requesting that the proposed implantation sites in the hair element 820 were to be based on the parameters of control points on the contour of, and within, the hair elements 820, 830 and 810, it will be apparent that some control points may be considered up to three times, if such control points are located in all three elements. Processing the interpolated value in this manner may lead to a proposed site plan in which the elements of overlap influence the interpolated value of site, giving an incorrect, distorted or undesirable value. This is particularly evident if density is the parameter of consideration. The treatment plan in this situation may be proposing a higher density value for proposed implantation site 960 than would be expected, potentially leading to a not so natural-looking hair transplant.

To address this issue, the present application proposes a solution. For example, each of the hair elements 810, 820 and 830 may be divided into multiple segments based on where they intersect with one another, and use a Boolean operator on those segments to reconstruct the real-estate or floor plan of the combination of the elements 810, 820 and 830 without the overlap. This is illustrated in FIG. 9b, in which the three elements 810, 820 and 830 are identified, element 810 equal to the sum of segments A, D, E and G; element 820 equal to the sum of segments B, E, F and G; and element 830 equal to the sum of segments C, D, F and G. If it is desired that implantation sites be proposed in all three hair elements 810, 820 and 830, an OR operator may be utilized, thus providing for interpolated values to be proposed within elements A+B+ C+D+E+F+G. However, if all desired hair has already been implanted into element 810, a difference (DIFF) operator can be used to exclude that area, thus providing for interpolated values to be proposed within elements B+C+F only. It will be apparent to the user that this approach facilitates a proposed implantation site plan in which the elements of overlap do not overly influence the interpolated value of implantation sites.

Figure 10:
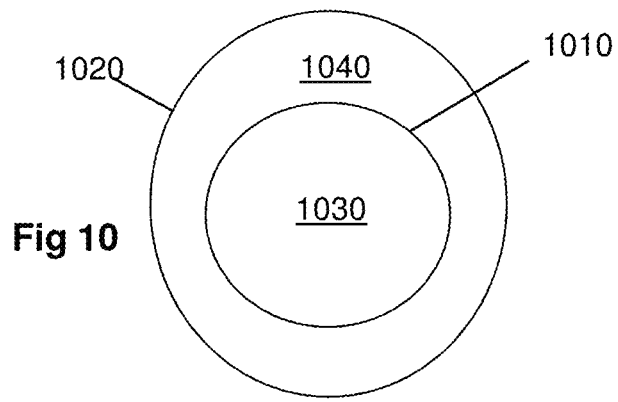
FIG. 10 illustrates an example of one hair element completely overlapping another hair element.

In some situations, a region of overlap may be one hundred percent, as illustrated in FIG. 10 in which element 1030 overlaps completely with another element which extends beyond the perimeter of element 830. This type of situation may result, for example, when the user has already implanted all desired hairs into the element denoted as 1030, and now wishes to extend coverage to the outer element denoted by 1040. A difference operator can once again be used such that interpolated values are only proposed for the element denoted 1040, and not the element 1030. In this manner more hairs are not implanted into element 1030, only into element 1040, in which hair have not yet been implanted. It is therefore possible to construct any shape for hair transplantation, opening up the opportunities for hair art, similar to tattoos, for example.

It should be noted that although the points which define the boundaries of the hair patch or the contour points, are all 3-dimensional (3-D) points in a 3-D coordinate system, in order to compute some of the formulae indicated above, and to calculate, for example, the polygon/element intersection, in one embodiment, the system may first project those 3-D contour points on a primary 2-dimensional (2-D) plane reconstructed using principle component analysis, a technique well-known to those in the art. Those projected 2-D polygons having coordinates in a 2-D coordinate system, may then be used for intersection computation. Once the computation has been completed, if required, the 2-D coordinates may be projected back into the 3-D coordinate system.

It will be appreciated that although the planning of implantation sites has been described above, the procedures can equally be applied to harvesting sites. The physician may identify harvesting elements from which hair is to be donated, along with associated control points, and request that, for example, the number of hairs in that identified element by reduced, reducing the number of hairs in such a way that the density is interpolated to be, for example, 80% of the pre-donated density value. The other implementations described throughout this application can equally be applied to harvesting.

Figure 11:
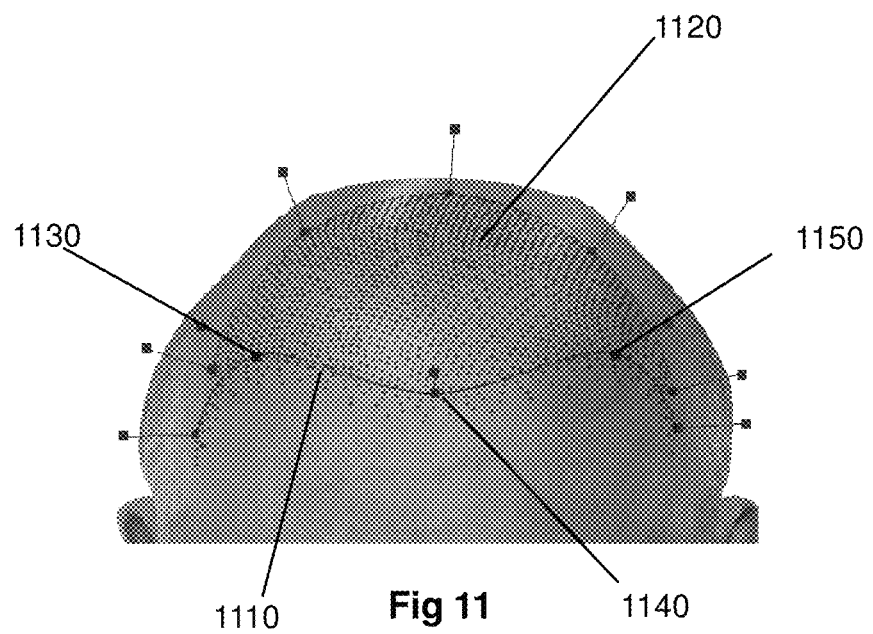
FIG. 11 illustrates an example of a proposed hairline adjacent to a proposed hair patch.

When front hairline 1110 and a hair element 1120 are placed close to each other (see FIG. 11), it is conceivable that the treatment planning system may only propose sites within the hair element 1120, and as such there will be a visible gap between the hairline 1110 and the boundary of the hair element 1120. Therefore, according to another aspect of the present application, the treatment planning system ensure that there is no space between them, or a least any space that does exist is natural looking, and conforms to the overall physical appearance of hair desired. In order to do this, the control points between neighboring or adjacent elements are shared. That is, the control points along the hairline 1110 and the boundary of the hair element 1120 that is adjacent to the hairline 1110 are shared. Hair link points are introduced for this purpose. To link the boundary of one hair element to another, the user may drag a control point on the boundary or perimeter of one hair element and dock it on a control point on the boundary or perimeter of the other hair element to "link" them. Disconnection, or the "un-sharing" of two control points may be accomplished by using, for example, another mouse button (right-click) and dragging to "separate" linked control points. The hair link points may be applied to hairlines, hair patches or the region between different hair elements. In the example illustrated in FIG. 11, there are three shared control points between front hairline 1110 and connected hair element (e.g. hair patch) 1120, namely control points 1130, 1140 and 1150. These control points link the hairline 1110 to the hair patch 1120. In this manner, when one of the shared control points 1130, 1140, or 1150 is updated (for example updating its position, direction, density, etc.), the linked control point on the other element, hair patch 1120 is also updated. That is, if the position of the hairline 1110 is moved, the system automatically updates the position of the boundary of the hair patch 1120 which adjacent to the hairline 1110. In this manner the user does not have the additional task of changing separately the hair patch 1120, and can concentrate on the planning process. This will also ensure that there is no gap and instead there is a smooth transition between close hairs that belong to different hair elements.

One of the factors that contribute to the successful outcome of a hair transplantation procedure is the natural-looking appearance of the front hairline. According to another aspect of the current application, method for generating a natural-looking hairline based on control points, and the techniques of modulation and interpolation are provided. These methods can be executed substantially automatically, or with assistance from the user.

Figure 12:
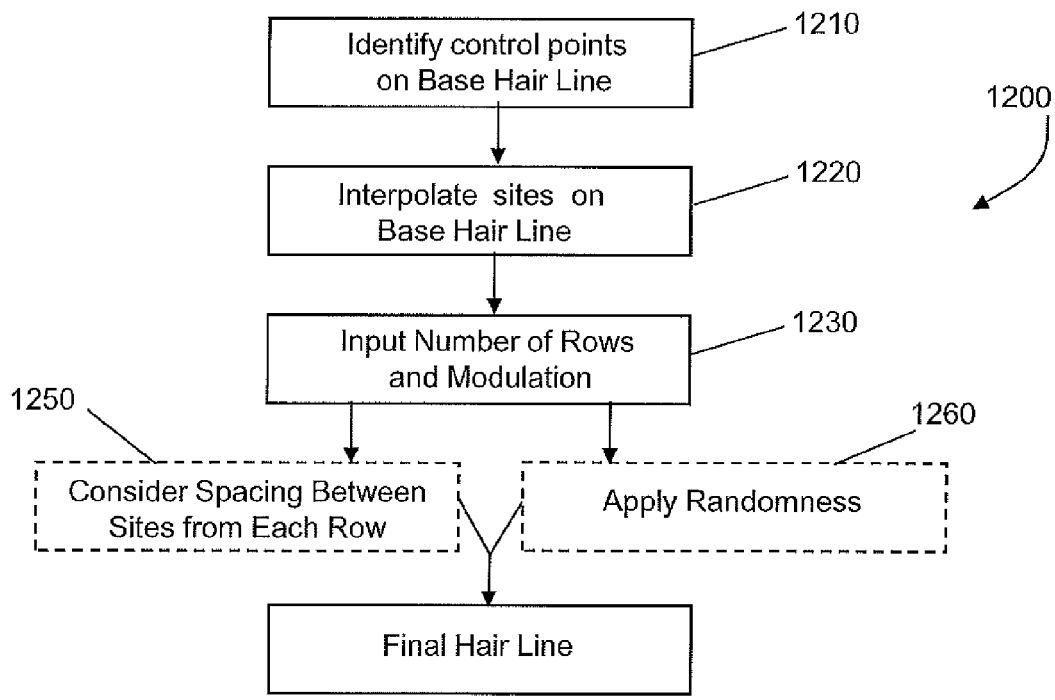
FIG. 12 is a flow chart illustrating an example of how interpolated sites can be generated for a hairline.

FIG. 12 is a flowchart illustrating an example process 1200 for generation of a proposed hairline comprising proposed implantation sites. Process 1200 is carried out by a device, such as an implementing module of the processing unit described above, and can be implemented in software, firmware, hardware, or a combination thereof. The process 1200 will be described in reference to FIGS. 12 and 13.

Figure 13:
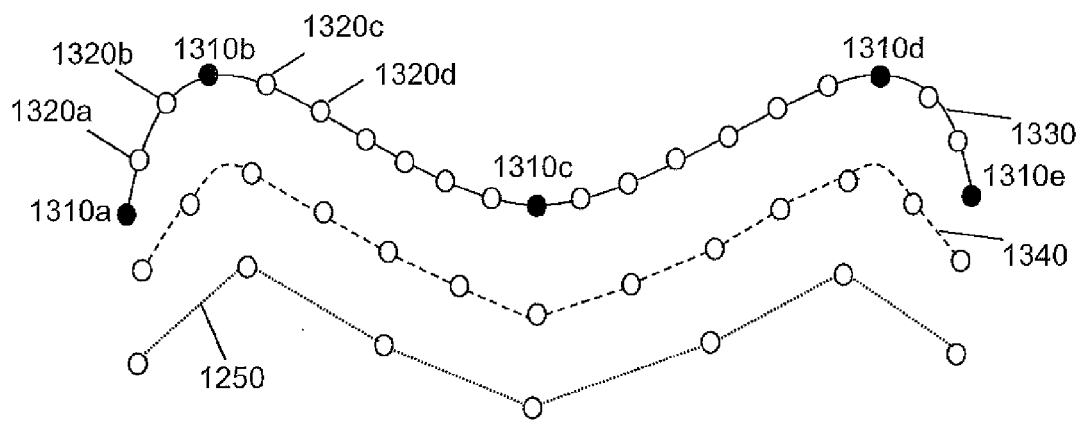
FIG. 13 depicts an example of an interpolated hairline.

Initially, in step 1210, control points are identified on the contour of a base hairline 1330 (as seen in FIG. 13), typically identified on what is to be the front row or curve of hair on the patient's head, in the direction of the patient's face, forming a hairline curve. These control points may be identified by the user through the user interface, and/or automatically proposed and generated by the treatment planning system. For purposes of explanation, FIG. 13 depicts such initial control points 1310*a*, 1310*b*, 1310*c*, 1310*d* and 1310*e*. These initial control points 1310*a*, 1310*b*, 1310*c*, 1310*d* and 1210*e* are used to generate a base hairline 1330 by any number of known techniques in which curves can be generated in the field of computer aided design, for example, by means of interpolation by a high-order interpolation algorithm such as Bezier interpolation or cubic interpolation. In this manner, an arbitrarily-shaped curve, based on a specified number of control points, in this example the five points 1310*a*, 1310*b*, 1310*c*, 1310*d* and 1310*e* will define the contour of the base hairline 1330. Once the initial base hairline has been proposed, the user may adjust the location and/or orientation of the control points interactively until the resulting base hairline 1330 is the desired curve that the user is seeking. In addition, the user may add additional control points, and/or adjust the density or spacing between the control points, or add a "randomness" factor, for example, as described in the U.S. Pat. No. 8,104,480.

Once the base hairline 1330 has been generated to the user's initial satisfaction, in step 1220, the respective location and direction of the follicular units to be implanted (1320*a*, 1320*b*, 1320*c*, 1320*d* etc.) along this base hairline 1330 are automatically determined by the planning module, along the curve, in order to complete the design of the base hairline 1330. The proposed implantation sites may be generated based on density, spacing and/or randomness parameters provided by the user through the user interface. Once again, if the proposed implantation sites are not to the user's satisfaction, the user may manipulate the control points to facilitate the desired changes in the interpolated implantation sites of the base hairline 1330. In some implementations, the interpolated sites of the base hairline may be created without first generating the hair curve on which the interpolated sites will reside.

When designing the front hairline or hairline, a physician typically uses more than one row of hair to define it. Therefore, designing a final hairline may comprise designing two or more rows of hair. In step 1230 of process 1200 for the generation of a proposed final hairline, the user may provide through the user interface the number of rows to be interpolated, and the modulation (that is, how the number of hairs in each subsequent row if reduced) from the base hairline 1330. As illustrated in FIG. 13, the user in this instance has requested the generation of two additional hairlines, and a modulation of about 70%. In this manner hairline 1340 is generated a pre-determined distance (provided by the user via the user interface, or automatically proposed by the planning module) from the base hairline 1330, comprising about 30% fewer proposed implantation sites than the hairline 1330. Also generated is hairline 1350 which has about 70% of number of proposed implantation sites of hairline 1340.

Before the final hairline design is proposed, the planning module may additionally execute further steps to aid in the creation of a natural-looking hairline. In step 1250, the spacing between any two neighboring implantation sites can be calculated, for example, a spacing between any two neighbor hairs in each of the rows 1330, 1340 and 1350, as well as the spacing between hairs located in neighbor rows (e.g. rows 1330 and 1340, or 1340 and 1350). If the proposed implantation sites are closer than the identified spacing provided by the user earlier, the location of the proposed implantation sites may be automatically adjusted to correct this. A randomness factor 1260 may additionally be applied. Having executed these additional steps, the result is a final hairline having a pre-determined number of rows of hair, modulation, and randomness factor.

Another of the factors that contribute to the successful outcome of a hair transplantation procedure is the natural-looking appearance of the density of hair throughout the patient's head. According to another aspect of the current application, methods (and corresponding processor systems) for generating a natural-looking interpolated density of implantation sites based on control points is provided. These methods can be executed substantially automatically, or with assistance from the user.

Figure 14:
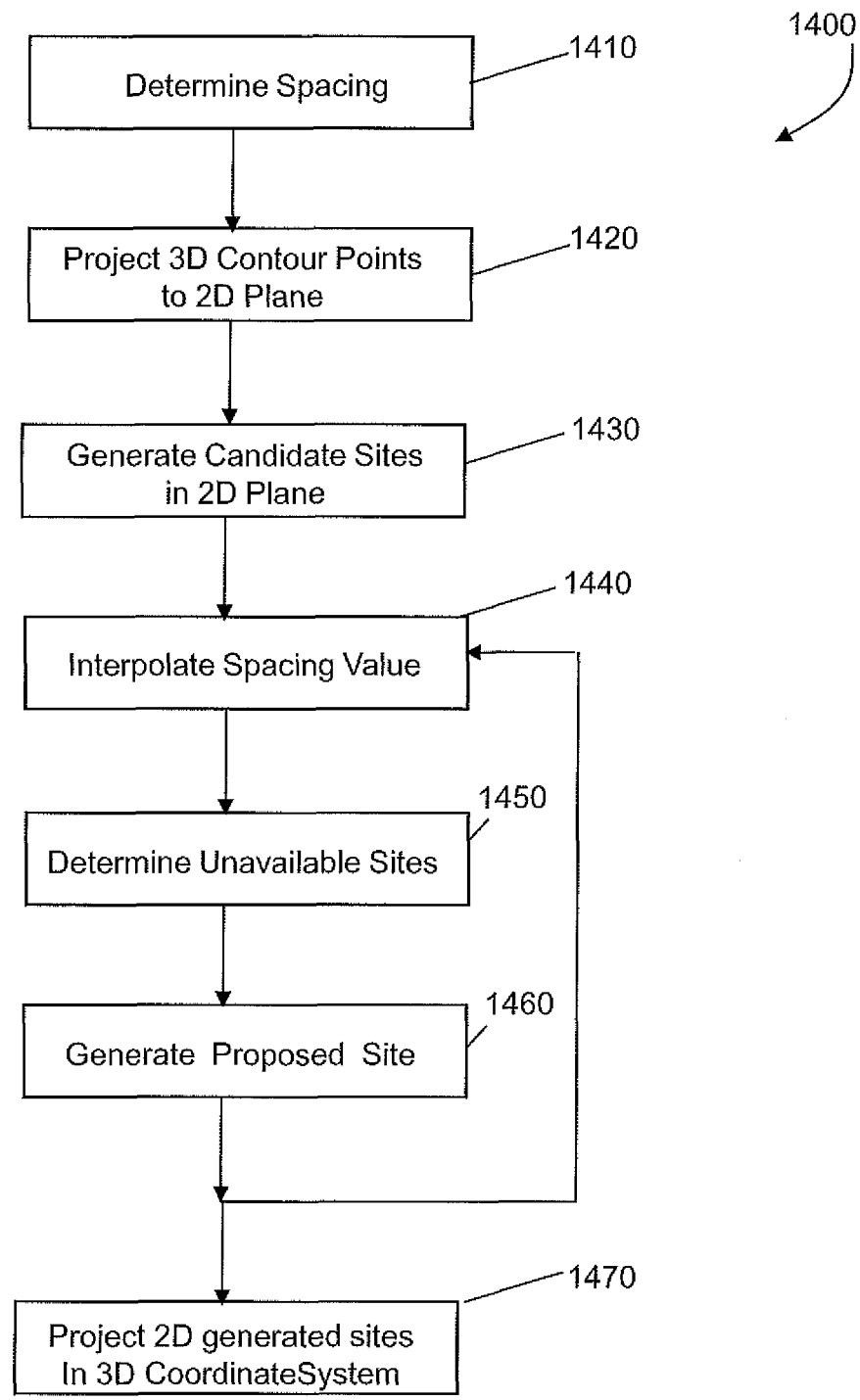
FIG. 14 is a flow chart illustrating an example of how sites can be generated within a hair boundary.

FIG. 14 is a flowchart illustrating an example process 1400 for generation of internal implantation sites based on density interpolation according to another aspect of the current application. Process 1400 is carried out by a device, such as an implementing module of the processing unit described above, and can be implemented in software, firmware, hardware, or a combination thereof. The process 1400, rather than trying to interpolate internal implantation sites in a 3-dimensional coordinate system, projects the 3-dimensional coordinates of a hair element into a 2-dimensional coordinate system and subsequently interpolates the internal implantation site in the 2-dimensional coordinate system. The interpolated internal implantation sites are then projected back into the 3-dimensional coordinate system, in which they are depicted on the 3-dimensional model of the patient. The example of the proposed process will be described in reference to FIGS. 14, 15 and 16.

One of the initial steps 1410 in the process 1400 is to determine spacing between proposed implantation sites for the hair element (e.g., hair patch) for which internal implantation sites are to be generated. There are numerous ways in which this can be determined, one of which, according to the present application, is converting density information (which may be provided via the user interface by the user, or calculated by a processing unit, for example) to spacing information. For example, assuming that the pattern of hair is simulated by triangles, one possible formula for the conversion of density to spacing information could be:

$$\text{Spacing} = \sqrt{\frac{200}{\text{Density} * \sqrt{3}}},$$

where the spacing of adjacent implantation sites from an implantation site is based on the Density of the implantation site which they are adjacent to. It will be appreciated that other formulations may be utilized and may be tailored to specific situations. For example, one may prefer to simulate a pattern of hair by squares rather than triangles perhaps, thus requiring the formula to be modified to reflect this information.

Figure 15:
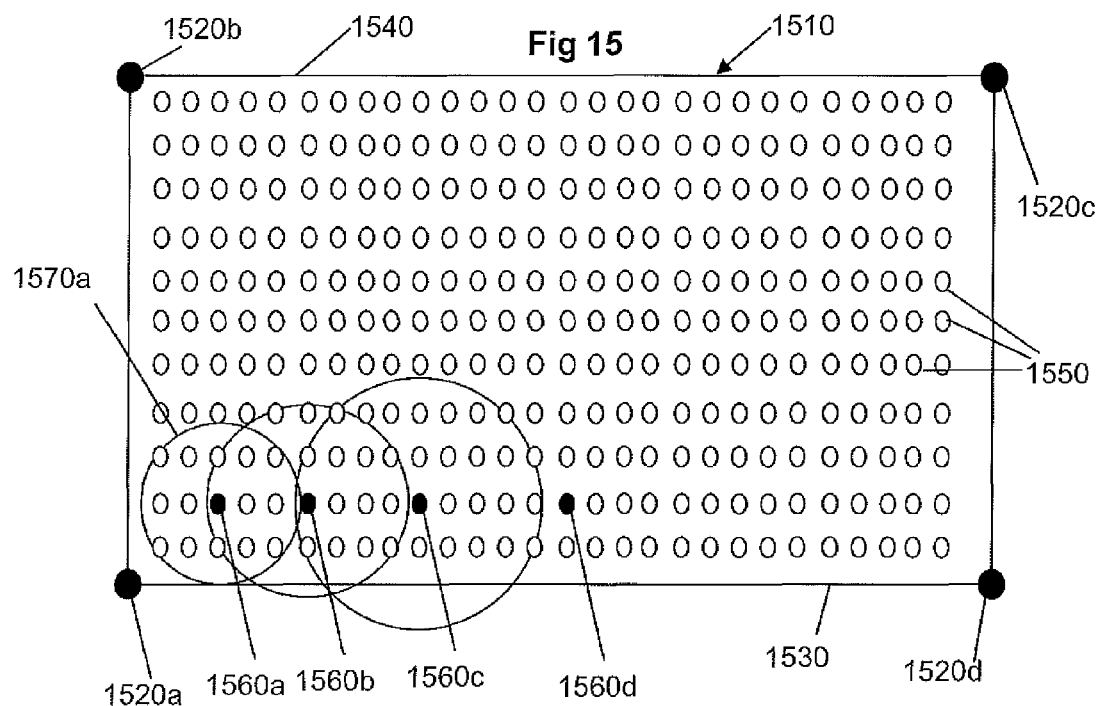
FIG. 15 illustrates one example of an embodiment of a 2-D projection of a hair patch.

Having determined the spacing information, a hair element in the form of a hair patch is identified. This hair patch comprises an outer boundary curve, which may be defined by one or more contour points. The hair patch may comprise conventional shapes such as circular, oval, polygonal or other such shapes, or be customized. Whatever the shape, it is intended that this identified hair patch will be on the patient's head, and as such will not comprise a flat surface, or 2-dimensional (2D) surface, but will comprise a 3-dimensional (3D) element. In this particular implementation of this aspect of the current application, step 1420 comprises projecting the 3D contour points which define the outer boundary curve in a 3D coordinate system, onto a 2D image in a 2D coordinate system. Methods for executing this step are well-known to those skilled in the art and will not be described herein. For ease in explanation, the resulting boundary curve 1510 and contour points 1520a, 1520b, 1520c and 1520d in the 2D coordinate system, as depicted in FIG. 15, will be used. In one implementation, the contour points may additionally comprise control points, the purpose of which will be described below.

Step 1430 comprises the generation of candidate implantation sites in the 2D coordinate system. Once again there are numerous implementations to accomplish this task that will be apparent to those skilled in the art. One of these is to identify a primary axis 1530, and to move in a direction away from the primary axis 1530, across the proposed internal implantation area towards the portion of the boundary curve 1510 on the other side of the internal implantation area (in FIG. 15, identified as 1540), creating or generating candidate sites 1550 which are depicted in FIG. 15 as white circular features. The primary axis 1530 is an arbitrary axis from which a direction can be proposed. In one embodiment the primary axis is positioned along or parallel to the longest dimension of the hair patch, thus requiring fewer "lines" of hairs to be proposed in the internal implantation area defined by the boundary curve 1510, and potentially requiring less processing time. The candidate sites 1550 represent a proposed site where a follicular unit could be implanted. The generation of candidate implantation sites in the 2D coordinate system may be based on a pattern of sites simulated by squares, as illustrated in FIG. 15, however, triangular placement, or any other such simulation pattern, is within the scope of this application.

Having generated candidate implantation sites in the 2D coordinate system, the planning module utilizes the formulation which determines the spacing between proposed implantation sites for the hair patch. However, to do this control points may be required. These control points may be discrete control points, or they may comprise, for example, the contour points as indicated above. In this particular example, let us assume that the contour points 1520a, 1520b, 1520c and 1520d serve additionally as control points, with control points 1520a and 1520b having associated density values of, for example 40 hairs per cm$^2$ and control points 1520c and 1520d having associated density values of, for example 20 hairs per cm$^2$. Along the primary axis 1530, the interpolated density values for each of the proposed implantation sites will therefore range from 40 hairs per cm$^2$ at 1520a to 20 hairs per cm$^2$ at 1520d, resulting in interpolated spacing value (step 1440), that is the spacing value between hairs being smaller at the end closest to 1520a (higher density), and larger at the end closest to 1520d (lower density). Each of the candidate implantation sites has an interpolated density value associated with it, and therefore, has a spacing value also associated with it, the spacing value representing the minimum spacing required to achieve the desired density interpolation value.

Referring to FIG. 15, based on the information derived from the control point 1520a, it may be determined that the candidate implantation site 1560a (shown as a black circular shape) is the closest candidate site which meets the spacing value criteria to achieve the desired interpolated value. The other candidate sites between the control point and the candidate implantation site 1560a being too close. Having established that candidate implantation sited 1560a is available for implantation, a virtual circle 1570a is drawn around the center 1560a, the diameter of the circle being determined by the spacing value formulation for this particular site, having an associated density value which has been determined by interpolation. Step (1450) aids in identifying those candidate sites that are unavailable for implantation. The candidate sites that fall within the circle 1570*a* are considered too close to proposed implantation site 1560*a*. The planning module is configured to execute operations that identify the next available candidate implantation site, in the same row as proposed implantation site 1560*a*, that is substantially parallel to the primary axis 1530 and within the hair region boundary curve 1510. As can be seen in FIG. 15, this is candidate implantation site 1560*b*, which now becomes a proposed implantation site, where it is intended that a follicular unit be implanted. As before, this proposed implantation site 1560*b* also has a spacing value associated with it, calculated from the formula indicated above, based on the associated density value which has been determined by interpolation. However, as indicated in FIG. 15, the spacing value is larger than that that was associated with proposed implantation site 1560*a*, and as can be seen, a virtual circle drawn around the proposed implantation site 1560*b* has a diameter that is larger than that drawn for proposed implantation site 1560*a*. Once again, the planning module is configured to execute operations that identify the next available candidate implantation site, in the same row as proposed implantation sites 1560*a* and 1560*b*, substantially parallel to the primary axis 1530 and within the hair region boundary curve 1510. As can be seen in FIG. 15, this is candidate implantation site 1560*c*, which now becomes a proposed implantation site, where it is intended that a follicular unit be implanted. This procedure is repeated along the row, and then the procedure initiated again as the next row of proposed implantation sites are identified, in a direction moving substantially parallel to, but away from the primary axis 1530, towards the opposite portion of the boundary curve 1510. In this manner all proposed implantation sites are identified and generated (Step 1460). It will be apparent from the description given above, that there will be more proposed implantation site identified and generated towards the high density end of the hair patch, the end where control point 1520*a* is located. Fewer proposed implantation sites will have been identified and generated towards the low density end of the hair patch, the end where control point 1520*d* is located.

Figure 16:
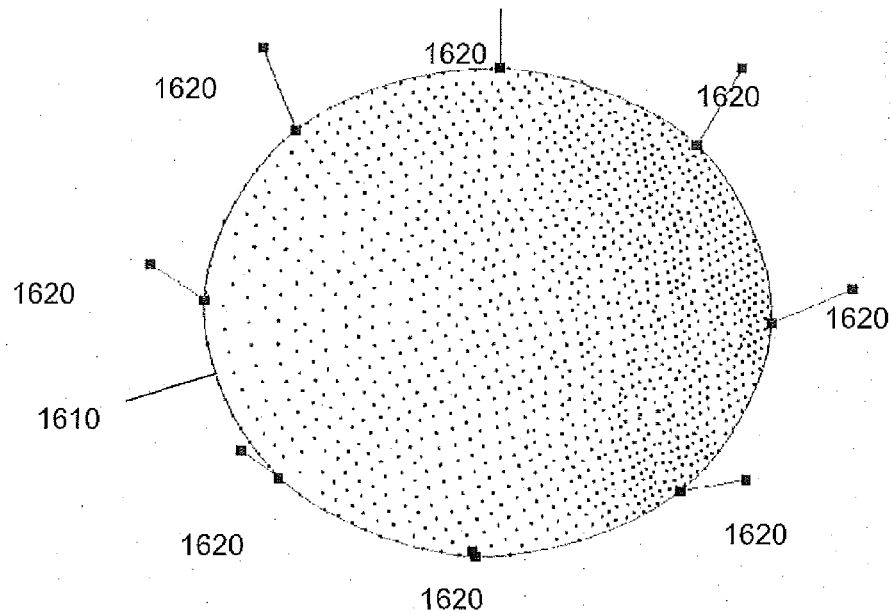
FIG. 16 illustrates another embodiment of a 2-D projection of a hair patch including proposed implantation sites.

The process is repeated, interpolating spacing values, determining unavailable site locations and generating proposed implantation site locations until the entire hair patch has been populated in this manner. The results of such a process are illustrated in FIG. 16, in which contour points 1620, which also serve as control points on the boundary curve 1610 provide for the proposed internal implantation sites to be generated.

Once the process has been completed, in step 1470, the 2D contour points which defined the outer boundary curve in a 2D coordinate system, and all the 2D coordinates of the proposed implantation sites (for example proposed implantation sites 1560*a*, 1560*b*, 1560*c* and 1560*d* are projected back into the 3D coordinate system. Once again, methods for executing this step are well-known to those skilled in the art and will not be described herein. In this manner, generation of internal implantation sites based on density interpolation is provided.

According to yet another aspect of the present application, additional methods and systems for improving treatment planning are provided. Having created a plan of proposed implantation sites, the treatment planning system may also be able to optimize the treatment process, by enabling the user to plan the number of procedures that may be required to obtain the desired result. As described in U.S. Pat. No. 8,388,631, a skin tensioner that can conform to a body surface and create tension, can be used to facilitate various procedures on the body surface, for example, harvesting of follicular units (FUs) from various locations on a body surface. These tensioning devices may come in various sizes and shapes and may be configured to conform to a particular element of the body surface.

Having generated and displayed on the user interface at least one implantation element (or region), but typically several implantation elements, the modeling software may utilize various algorithms to generate and overlay a representation of one or more region locators or, in some embodiments, skin tensioners to cover the proposed implantation or treatment area. The region locators may be used to hold fiducials or markers for directing image-guided systems that may be used in implementing various methods according to the present disclosure. The optimization algorithm may also operate to minimize the total number of tensioners to be used in the treatment procedure, minimize the overlay area between tensioners, and/or potentially reduce the number of sessions a patient is required to undergo.

To facilitate this, the user may be required to provide some constraints for the region locator or tensioner placement, such as for example, the maximum number of region locators or tensioners they would like to use in the procedure, the type of tensioner, the size of the tensioner, etc. This could be done via the user interface. Optionally, the user can manually adjust a plan that may be generated by the computer, indicating the number and placement of tensioners proposed to be adopted by the user in executing the proposed treatment plan. For example, the user may adjust the proposed locations of the tensioners to perhaps avoid aggravating existing scars, perhaps.

Figure 17A:
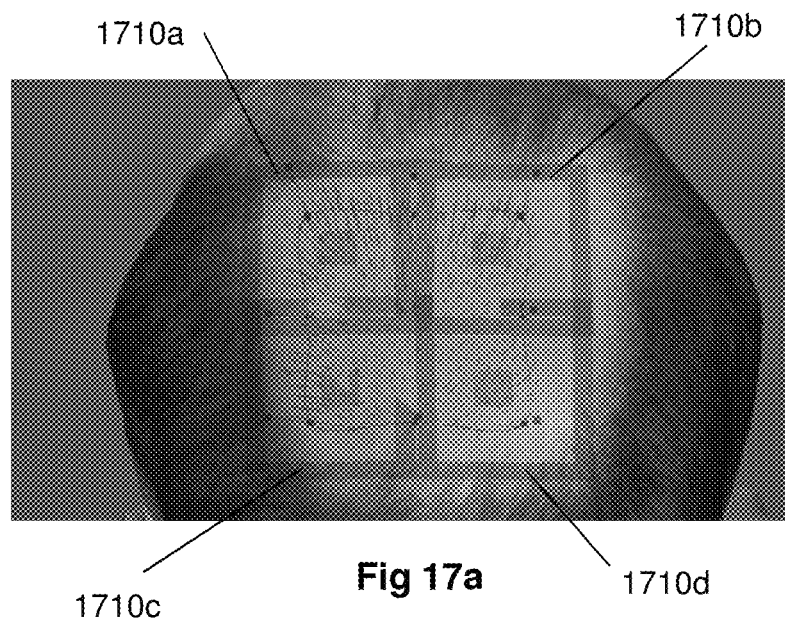
FIGS. 17a and 17b illustrate a representation of the patient's head, including hair regions with proposed implantation sites, and tensioning device representations.
Figure 17B:
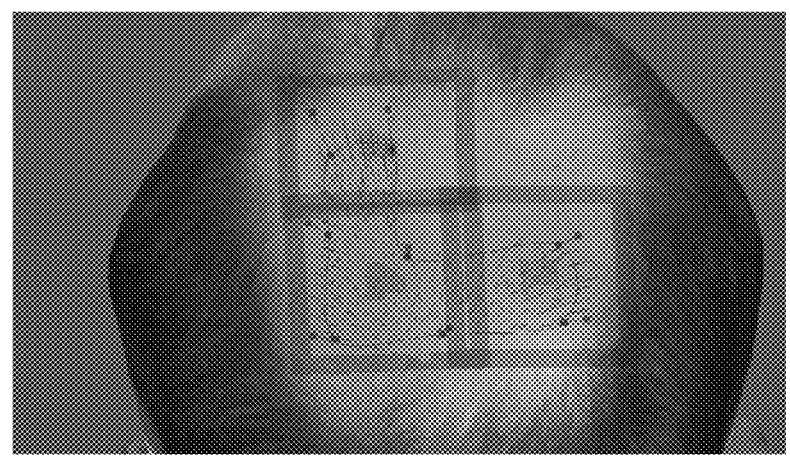

FIGS. 17*a* and 17*b* illustrate the overlay of tensioners that may be generated to enable the user to execute two different treatment plans. In FIG. 17*a*, the proposed implantation element(s) span an area that substantially occupies the bald area of the patient's scalp and requires the use of four (4) tensioners 1710*a*, 1710*b*, 1710*c* and 1710*d*. On the other hand, in FIG. 17*b*, the proposed implantation element(s) spans a lesser area, requiring only three (3) tensioners.

It will be apparent to those skilled in the art, that there are many algorithms that may be utilized to provide such functionality. In one example of this aspect of the current application, the processing unit may determine the outer contour of the combined hair elements, and based on that information, and the size of the tensioner, place one or more representations of the tensioner such that the entire area within the outer contour is covered by tensioners. In one embodiment of this aspect of the current application, the processing unit may remove from consideration any virtual tensioner which encompasses an area with no or a predetermined limited number of proposed implantation sites.

In another example of this aspect of the current application, the area covered by the combined hair elements can be virtually divided into grid sections, and a linear algebra cost function may be utilized to optimize the coverage of the grid points. Utilizing a set of one or more parameters, including but not limited, for example, to the number of tensioners, the location of tensioner and the size of tensioners, a value can be assigned which represents an objective value of any particular combination of values of the parameters in question. The objective value may vary depending upon which of the one or more parameters is weighted most highly, or has more value in any particular situation. For example, even though the use of fewer large tensioners may be possible for a particular treatment plan, the values may be configured such that smaller tensioners have a greater value, and as such the objective value may be found to be higher in that situation. This would, for example, be the case where the treatment plan was to be carried out on a child, or a patient with a small head, and it would be easier to utilize the smaller sized tensioner or region locator rather than the larger ones.

When utilizing this aspect of the current application, the treatment plan therefore comprises the treatment plan in terms of the proposed site locations/orientations, and the location/orientation of tensioners. Once the full plan meets the expectation of the physician, user and/or the patient, the user may then register the treatment plan with an actual patient. In some embodiments, this may be accomplished by using one or more cameras to identify one or more markers on the patient or a device on the patient. The marker may be a reflector that is secured to the patient, an ink mark drawn on the patient, an anatomy of the patient, the tensioner itself (or any portion thereof). Alternatively the marker may be a marking on a body surface tensioning device utilized by the physician in the hair transplantation procedure. The identified marker(s) may be used to determine a position and/or orientation of the implantation region of on the patient. Fiducial detection algorithms may be used to locate and refine the position of these markers. It will be apparent that the closer the fiducials/reference markers are to the proposed implantation area, the more accurate the registration of the treatment plan will be to the patient.

It will be apparent that although the methodology described above as discrete steps, one or more steps may be combined or even deleted, without departing from the intended functionality of the embodiments of the application. It will also be apparent that the methods described above may be performed manually, or they may be partially or substantially automated, including performed using robotic systems. Although described in a manner indicating that hair is harvested from and implanted into the same patient, hair can similarly be harvested from one patient and implanted into another. Alternatively, hair can be received from another source and implanted.

The foregoing illustrated and described embodiments of the application are susceptible to various modifications and alternative forms, and it should be understood that the applications as generally disclosed herein, as well as the specific embodiments described herein, are not limited to the particular forms or methods disclosed, and that many other embodiments are possible within the spirit and the scope of the present applications. Moreover, although individual features of one embodiment may be discussed herein or shown in the drawings of the one embodiment and not in other embodiments, it should be apparent that individual features of one embodiment may be combined with one or more features of another embodiment or features from a plurality of embodiments. By way of non-limiting example, it will be appreciated by those skilled in the art that particular features or characteristics described in reference to one figure or embodiment may be combined as suitable with features or characteristics described in another figure or embodiment. Furthermore, the methodologies described can be applied to any treatment, and is not limited to hair transplantation.

It will be further appreciated by those skilled in the art that the application is not limited to the use of a particular system, and that automated (including robotic), semi-automated, and manual systems and apparatus may be used for positioning and actuating the respective removal tools and other devices and components disclosed herein.

While the application has been described in its preferred embodiments, it is to be understood that the words which have been used are words of description and not of limitation. Therefore, changes may be made within the appended claims without departing from the true scope of the application.

What is claimed is:

1. A method of planning for transplantation of follicular units in a body surface, comprising:
   generating and displaying on a three-dimensional model of a body surface, at least two hair elements, each of the respective hair elements comprising one or more control points, the one or more control points having corresponding parameters associated therewith;
   associating, with a use of a processor, a first and a second of the at least two hair elements with each other to form a hair group; and
   generating or modifying at least one site within or on the first hair element, based at least in part on the parameters of at least one of the one or more control points of the second hair element.

2. The method of claim 1, wherein the at least one site is a harvesting site, an incision making site, or an implantation site.

3. The method of claim 1, the method comprising displaying the at least one site on the three-dimensional model.

4. The method of claim 1, wherein the step of generating or modifying the at least one site is based on the parameters of at least one of the one or more control points from each of the hair elements of the hair group.

5. The method of claim 1, wherein the hair element comprises a hairline, a boundary curve or a hair patch.

6. The method of claim 1, the method further comprising allowing a user to select hair elements that are associated to form a hair group.

7. The method of claim 1, wherein the hair element can be modified by a user.

8. The method of claim 1, wherein hair element is a hair patch, and the one or more control points are located inside a periphery of the hair patch.

9. The method of claim 1, wherein the parameters comprise one or more of a location of one or more hair elements, a geometric profile of hair elements, a number and/or type of follicular units to be harvested/implanted, a degree of randomness associated with particular harvest/implant locations, a spacing between adjacent implant locations, a depth of follicle, a depth of implant, an orientation of follicles or follicular units, a patient identification, a marker location, or a density of harvest/implant sites.

10. The method of claim 1, wherein one of the parameters is density, and the density associated with the at least one site is based at least in part on an inverse transform algorithm between the at least one site and at least one of the one or more control points of the set of control points.

11. The method of claim 1, wherein a value of a parameter associated with the at least one site is a weighted value based at least in part on the corresponding values of such parameter of the set of control points.

12. The method of claim 1, wherein the at least two hair elements at least partially overlap, and the proposed follicular unit implantation sites are automatically modified or generated such that a density of proposed follicular unit sites in an area of overlap is substantially similar to a density of other proposed follicular unit sites within a non-overlapping portion of the first or the second element.

13. The method of claim 1, the method comprising selecting a first control point from the first hair element and a second control point from the second hair element, and linking the first and second selected control points such that modification of the first selected control point automatically modifies the second selected control point.

14. The method of claim 1, the method further comprising performing a procedure on the at least one site according to the planning.

15. The method of claim 1, the method comprising directing an automated system for hair transplantation to execute the plan to harvest, make sites, or implant follicular units in the body surface.

16. The method of claim 1, the method comprising generating one or more virtual grid sections corresponding to placement of a skin tensioning or a fiducial locator device on the body surface according to the plan.

17. The method of claim 16, wherein the one or more virtual grid sections are generated based on an outer contour of the at least two hair elements.

18. The method of claim 16, wherein the one or more virtual grid sections are generated at least partially based on a size of a skin tensioning device.

19. The method of claim 1, the method further comprising transferring the treatment plan to a robotic system for performing the treatment plan.

20. A system for planning for transplantation of follicular units in a body surface, comprising:
a user interface including a user input device,
at least one non-transitory storage medium storing instructions, and
a processor comprising one or more modules for executing operations on image data, the one or more modules comprising instructions for:
generate and display on a three-dimensional model of a body surface, at least two hair elements, each of the respective hair elements comprising one or more control points, the one or more control points having corresponding parameters associated therewith;
associating a first and a second of the at least two hair elements with each other to form a hair group; and
generating or modifying at least one site within or on the first hair element, based at least in part on the parameters of at least one of the one or more control points of the second hair element.

21. The system of claim 20, wherein the one or more of control points is user selected, automatically generated, or a combination of both.

22. The system of claim 20, wherein the processor is further configured to process images of the body surface to generate the three-dimensional body surface.

23. The system of claim 20, further comprising an image repository.

24. The system of claim 20, wherein a value of a parameter associated with the at least one site is a weighted value based at least in part on the corresponding values of such parameter of the control points.

25. The system of claim 20, wherein the processor is further configured to select a first control point from the first hair element and a second control point from the second hair element, and linking the first and second control points such that modification of the first selected control point automatically modifies the second selected control point.

26. The system of claim 20, further comprising an imaging device.

27. The system of claim 20, wherein the at least one processor further executes instructions to generate one or more virtual grid sections corresponding to placement of a skin tensioning device or a fiducial locator device that may be used to execute the treatment plan.

28. A method of planning for transplantation of follicular units in a body surface, comprising:
generating and displaying on a three-dimensional model of a body surface, at least two hair elements, each of the respective hair elements comprising one or more control points, the one or more control points having corresponding parameters associated therewith, wherein the parameters comprise one or more of a location of one or more hair elements, a geometric profile of hair elements, a number and/or type of follicular units to be harvested/implanted, a degree of randomness associated with particular harvest/implant locations, a spacing between adjacent implant locations, a depth of follicle, a depth of implant, an orientation of follicles or follicular units, a patient identification, a marker location, or a density of harvest/implant sites;
associating, with a use of a processor, a first and a second of the at least two hair elements with each other to form a hair group; and
generating or modifying at least one site within or on the first hair element, based at least in part on the parameters of at least one of the one or more control points of the second hair element.

29. The method of claim 28, wherein the at least two hair elements are selected from a repository comprising templates.

30. The method of claim 28, wherein the at least two hair elements are generated based on an image data.

31. The method of claim 28, further comprising projecting locations of the one more control points onto a two-dimensional plane, generating or modifying the at least one site in the two-dimensional plane, and projecting the two-dimensional location of the generated or modified site back onto the three-dimensional model of the body surface.

32. A system for planning for transplantation of follicular units in a body surface, comprising:
a user interface including a user input device,
at least one non-transitory storage medium storing instructions, and
a processor comprising one or more modules for executing operations on image data, the one or more modules comprising instructions for:
generate and display on a three-dimensional model of a body surface, at least two hair elements, each of the respective hair elements comprising one or more control points, the one or more control points having corresponding parameters associated therewith, wherein a value of a parameter associated with the at least one site is a weighted value based at least in part on the corresponding values of such parameter of the control points;
associating a first and a second of the at least two hair elements with each other to form a hair group; and
generating or modifying at least one site within or on the first hair element, based at least in part on the parameters of at least one of the one or more control points of the second hair element.

33. The system of claim 32, further comprising a repository of templates.

* * * * *